(12) United States Patent
Kobilka et al.

(10) Patent No.: US 11,021,425 B2
(45) Date of Patent: Jun. 1, 2021

(54) POLYBROMINATED DIPHENYL-BASED FLAME RETARDANT COMPOUNDS

(71) Applicant: International Business Machines Corporation, Armonk, NY (US)

(72) Inventors: Brandon M. Kobilka, Tucson, AZ (US); Scott B. King, Rochester, MN (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 56 days.

(21) Appl. No.: 16/158,374

(22) Filed: Oct. 12, 2018

(65) Prior Publication Data

US 2020/0115308 A1    Apr. 16, 2020

(51) Int. Cl.
*C07C 41/18* (2006.01)
*C07C 45/47* (2006.01)
(Continued)

(52) U.S. Cl.
CPC .............. *C07C 41/18* (2013.01); *C07C 45/46* (2013.01); *C07C 45/47* (2013.01); *C07C 217/90* (2013.01);
(Continued)

(58) Field of Classification Search
CPC ....................................................... C07F 1/08
See application file for complete search history.

(56) References Cited

U.S. PATENT DOCUMENTS

| 6,197,864 B1 | 3/2001 | Borke et al. |
| 7,405,254 B2 | 7/2008 | Muylem et al. |

(Continued)

FOREIGN PATENT DOCUMENTS

WO    1997047663 A1    12/1997

OTHER PUBLICATIONS

Sun et al. ("Synthesis of Br7-Br9 hydroxylated/methoxylated polybrominated diphenyl ethers (OH/MeO-PBDEs) and analyses on mass spectra and GC data of the MeO-PBDEs" Chemosphere, 92, 2013, 286-292). (Year: 2013).*

(Continued)

*Primary Examiner* — Peter F Godenschwager
(74) *Attorney, Agent, or Firm* — Kelsey M. Skodje

(57) ABSTRACT

A process of forming a flame retardant material is disclosed. The process includes forming a functionalized polybrominated diphenyl-based flame retardant compound having the following structural formula:

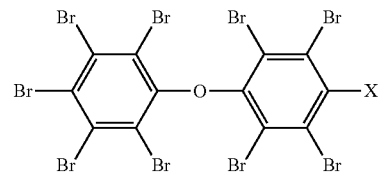

In the structural formula, X corresponds to a functional group. The process also includes forming a flame retardant material by covalently bonding the functionalized polybrominated diphenyl-based flame retardant compound into a material using the functional group.

20 Claims, 34 Drawing Sheets

(51) Int. Cl.
  C07C 45/46    (2006.01)
  C07C 217/90   (2006.01)
  C07C 321/12   (2006.01)
  C07F 1/08     (2006.01)
  C07D 303/08   (2006.01)
  C07C 321/28   (2006.01)
  C07C 49/84    (2006.01)
  C07C 43/225   (2006.01)
  C07C 43/23    (2006.01)

(52) U.S. Cl.
  CPC .......... *C07C 321/12* (2013.01); *C07C 321/28* (2013.01); *C07D 303/08* (2013.01); *C07F 1/08* (2013.01); *C07C 43/225* (2013.01); *C07C 43/23* (2013.01); *C07C 49/84* (2013.01)

(56) References Cited

U.S. PATENT DOCUMENTS

| | | |
|---|---|---|
| 8,367,754 B2 | 2/2013 | Lee et al. |
| 8,507,594 B2 | 8/2013 | Kwon et al. |
| 8,883,316 B2 | 11/2014 | Su |
| 9,228,131 B2 | 1/2016 | Biscoglio |
| 2017/0002131 A1 | 1/2017 | Zeng et al. |

OTHER PUBLICATIONS

Teclechiel et al., *Synthesis of polybrominated diphenyl ethers via symmetrical tetra- and hexabrominated diphenyliodonium salts*, Chemosphere 74, Issue 3, Nov. 2008, pp. 421-427, Elsevier B.V., Amsterdam.

Sun et al., *Synthesis of Br7—Br9 hydroxylated/methoxylated polybrominated diphenyl ethers (Oh/MeO-PBDEs) and analyses on mass spectra and GC data of the MeO-PBDEs*, Chemosphere, vol. 92, Issue 3, Jul. 2013, pp. 268-292, Elsevier B.V., Amsterdam.

Smith et al., *Synthesis and reactions of some pentabromophenyl organometallics*, Journal of Organometallic Chemistry, vol. 42, Issue 2, Sep. 1972, pp. 257-265, Elsevier Sequoia S.A, Lausanne.

Smith et al., *Improved synthesis of pentabromophenylmagnesium bromide and 1,2,4,5-tetrabromophenylbis(magnesium bromide)*, Journal of Organometallic Chemistry, vol. 33, Issue 2, Dec. 1971, pp. C21-C24, Elsevier B.V., Amsterdam.

Teclechiel et al., *Synthesis of Octabrominated Diphenyl Ethers from Aminodiphenyl Ethers*, Environmental Science & Technology, Oct. 2007, vol. 41, Issue 21, pp. 7459-7463, American Chemical Society, Washington, D.C.

Mo et al., *Bioaccumulation of Polybrominated Diphenyl Ethers, Decabromodiphenyl Ethane, and 1,2-Bis(2,4,6-Tribromophenoxy) Ethane Flame Retardants in Kingfishers (Alcedo atthis) From an Electronic Waste-Recycling Site in South China*, Environmental Toxicology and Chemistry, vol. 31, Issue 9, Sep. 2012, pp. 2153-2158, Society of Environmental Toxicology and Chemistry (SETAC) Press, USA.

Christiansson et al., *Methods for synthesis of nonabromodiphenyl ethers and a chloro-nonabromodiphenyl ether*, Chemosphere, vol. 63, Issue 4, Apr. 2006, pp. 562-569, Elsevier, Amsterdam.

Sonogashira Related SciFinder Results, Received: Feb. 2, 2018, 3 pages.

Bretler et al., "Synthesis and characterization of poly(pentabromostyrene) micrometer-sized particles of narrow size distribution for flame-retardant applications," Colloid and Polymer Science, 292, 2014, 1181-1189, (Abstract Only).

Shishkin et al., "Cross coupling of polybromoiodobenzenes with some terminal alkynes," Russian Journal of Organic Chemistry, 44, 2008, 1323-1326, (Abstract Only).

\* cited by examiner

210

620

900

POLYBROMINATED DIPHENYL-BASED FLAME RETARDANT COMPOUNDS

BACKGROUND

Brominated flame retardants include polybrominated diphenyl ethers (PBDEs), decabromodiphenyl ethane (DBDPE), and 1,2-bis(2,4,6-tribromophenoxy) ethane (BTBPE). There is a trend toward reducing or eliminating such polybrominated diphenyl-based flame retardant compounds because they bio-accumulate when they "leach out" (e.g., in electronic waste recycling).

SUMMARY

According to an embodiment, a process of forming a flame retardant material is disclosed. The process includes forming a functionalized polybrominated diphenyl-based flame retardant compound having the following structural formula:

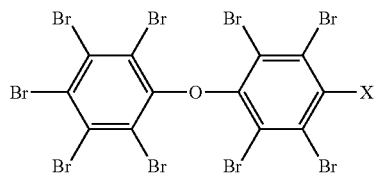

In the structural formula, X corresponds to a functional group. The process also includes forming a flame retardant material by covalently bonding the functionalized polybrominated diphenyl-based flame retardant compound into a material using the functional group.

According to another embodiment, process of forming a polybrominated flame retardant compound is disclosed. The process includes forming an organocuprate compound having the following structural formula:

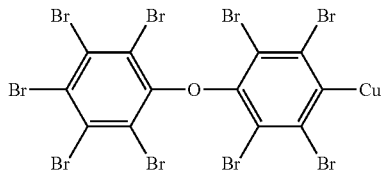

The process also includes utilizing the organocuprate compound to form a polybrominated flame retardant ketone compound having the following structural formula:

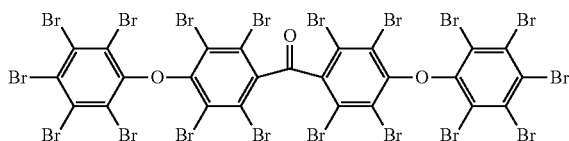

According to yet another embodiment, an organocuprate compound is disclosed having the following structural formula:

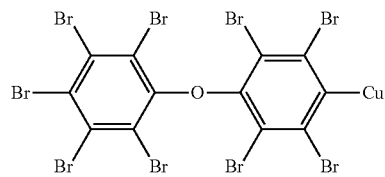

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes functionalized polybrominated diphenyl-based flame retardant compounds and processes for forming such functionalized polybrominated diphenyl-based flame retardant compounds. The functionalized polybrominated diphenyl-based flame retardant compounds of the present disclosure include one or more functional groups to enable covalent bonding to a material in which it is embedded, thereby mitigating "leach out" associated with existing polybrominated diphenyl-based flame retardant compounds, such as polybrominated diphenyl ethers and polybrominated diphenyl ethanes.

The present disclosure depicts examples of reactions and synthetic schemes to form various functionalized polybrominated diphenyl ether (PBDE) compounds. In general, the various PBDE compounds of the present disclosure correspond to nona-brominated diphenyl ether compounds, substituting a single functional group for a single bromine group of a deca-brominated diphenyl ether compound (see e.g. FIGS. 1, 2A-2D, 3A-3D, 4A-4D, 5B-5C and 5E, 6A-6D, 8A-8B, 9A-9B, and 10A-10B). However, it will be appreciated that the various PBDE compounds of the present disclosure may have an alternative number and/or arrangement of functional groups and/or bromine groups.

In addition, it will be appreciated that similar reactions and synthetic schemes may be used to form functionalized polybrominated diphenyl ethane compounds. As an illustrative, non-limiting example, a mono-functionalized nona-brominated diphenyl ethane compound may have the following generic structural formula:

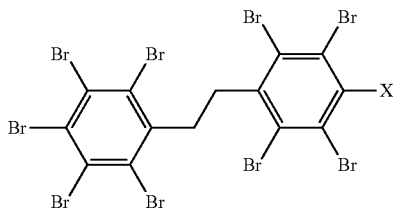

In the above generic structural formula, X may represent various functional groups for covalently bonding the polybrominated diphenyl ethane compound to a material in which they are embedded. In some cases, as described further herein, X may be bonded to an alternative carbon of the phenyl ring. In other cases, as described further herein, the other phenyl ring may also be functionalized with an X group, representing an example of a di-functionalized octa-brominated diphenyl ethane compound. Thus, the present disclosure encompasses polybrominated diphenyl ethane compounds having an alternative number and/or arrangement of functional groups and/or bromine groups.

Figure 1:
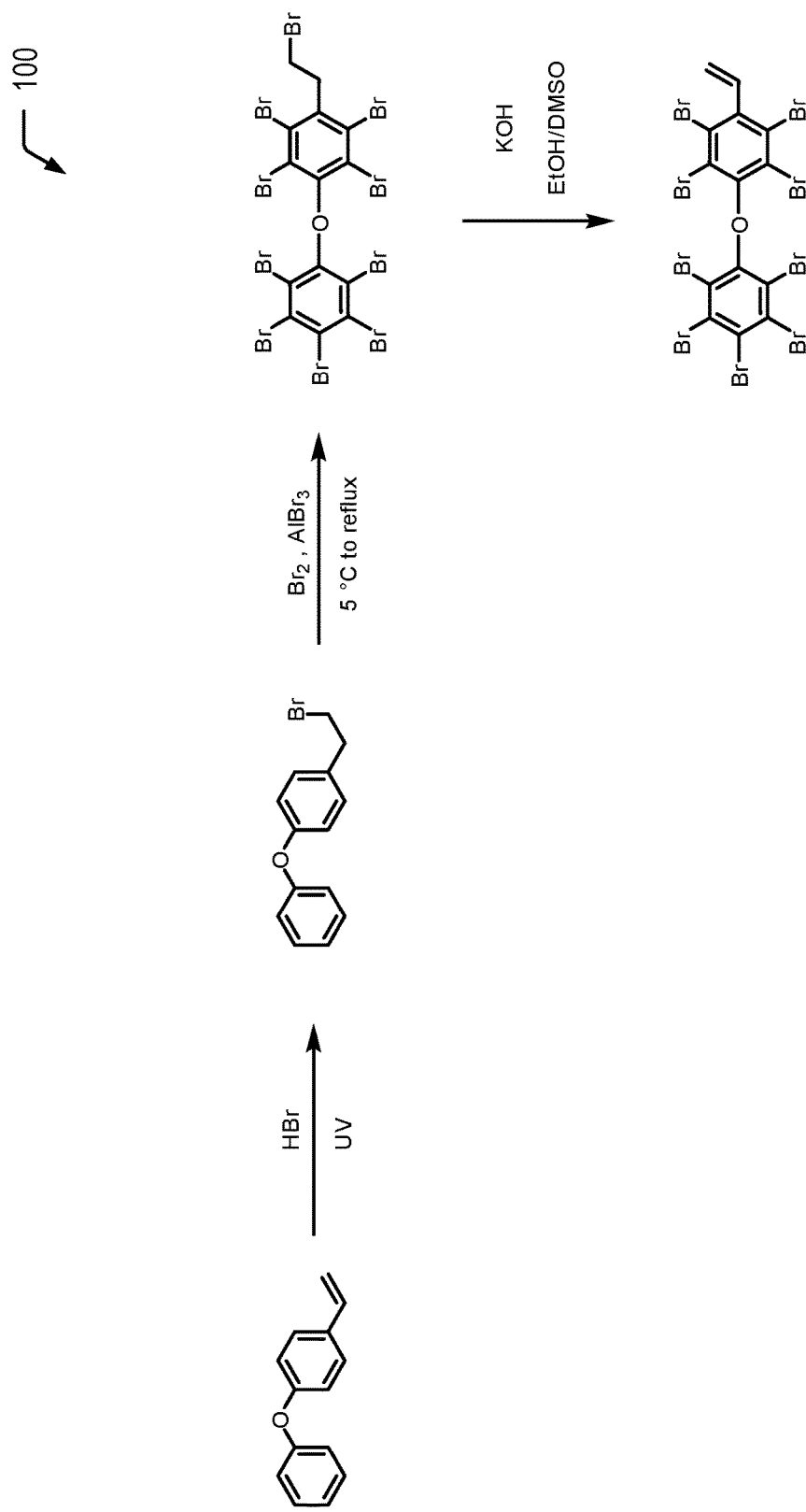
FIG. 1 is a chemical reaction diagram illustrating a process for forming a vinyl-polybrominated diphenyl ether (Vinyl-PBDE) compound, according to a particular embodiment.

Referring to FIG. 1, a chemical reaction diagram 100 illustrates an example of a process of forming a vinyl-polybrominated diphenyl ether (Vinyl-PBDE) compound, according to a particular embodiment.

In the first chemical reaction of FIG. 1, a vinyl-functionalized diphenyl ether compound is utilized to form a brominated diphenyl ether compound. In the particular embodiment depicted in FIG. 1, the vinyl-functionalized diphenyl ether compound is 4-vinyldiphenyl ether (IUPAC name 1-ethenyl-4-phenoxybenzene). The first chemical reaction of FIG. 1 illustrates that the vinyl group of the 4-vinyldiphenyl ether compound is brominated to form a brominated diphenyl ether compound having the following structural formula:

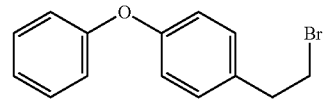 [SMILES: BrCCc1ccc(Oc2ccccc2)cc1]

As a prophetic example, the vinyl group of the 4-vinyldiphenyl ether compound may be brominated using HBr via a UV-promoted anti-Markovnikov reaction to form the brominated diphenyl ether compound depicted in FIG. 1.

It will be appreciated that the 4-vinyldiphenyl ether compound depicted in FIG. 1 is one example of a vinyl-functionalized diphenyl ether compound and that the vinyl group may be positioned at an alternative location on the phenyl ring. Examples of such alternative vinyl-functionalized diphenyl ether compounds include 1-ethenyl-3-phenoxybenzene and 1-ethenyl-2-phenoxybenzene. Further, it will further be appreciated that alternative vinyl-functionalized diphenyl ether compounds containing vinyl groups on both phenyl rings may be also utilized. Examples of alternative vinyl-functionalized diphenyl ether compounds include 1,1'-Oxybis(4-ethenylbenzene) and 1,1'-Oxybis(2-ethenylbenzene).

The second chemical reaction of FIG. 1 illustrates that the brominated diphenyl ether compound is subsequently polybrominated using bromination methods similar to those used to synthesize a decabromodiphenyl ether compound, resulting in a PBDE compound with an alkylbromide group having the following structural formula:

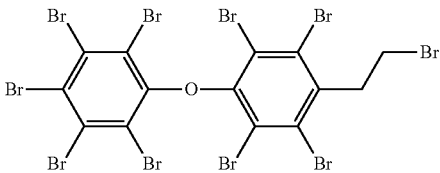

As a prophetic example, the brominated diphenyl ether compound in bromine may be added dropwise to a solution of aluminum tribromide in bromine under reflux and vigorous stirring. The mixture may be refluxed for 3 hours and excess bromine may be removed with a gentle steam of nitrogen. The residue may be washed with water, sodium hydroxide, and aqueous 5% sodium disulfite. The solid product may be dissolved in toluene and washed with water. The organic phase may be evaporated leaving a solid of the PBDE compound with the alkylbromide group, which may be subsequently purified according to various techniques known to one of ordinary skill in the art.

The third chemical reaction of FIG. 1 illustrates that the alkylbromide group of the PBDE compound is then eliminated to reconstitute the double bond, yielding a vinyl-PBDE compound having the following structural formula:

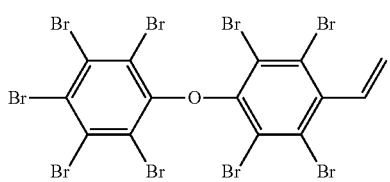 [SMILES: C=Cc1c(Br)c(Br)c(Oc2c(Br)c(Br)c(Br)c(Br)c2Br)c(Br)c1Br]

As a prophetic example, a solution of potassium hydroxide and anhydrous ethanol may be added to a refluxing slurry of the PBDE compound with the alkylbromide group and anhydrous ethanol. After refluxing for 2 hours, the reaction mixture may be filtered hot and the filter cake may be washed with water and dried under reduced pressure, which may be subsequently purified according to various techniques known to one of ordinary skill in the art.

As noted above, an alternative to the 4-vinyldiphenyl ether starting material is 1,1'-Oxybis(4-ethenylbenzene). In this case, for a similar reaction scheme, an octa-brominated diphenyl ether compound with multiple vinyl groups may be formed, having the following structural formula:

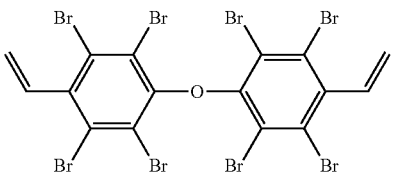 [SMILES: C=Cc1c(Br)c(Br)c(Oc2c(Br)c(Br)c(C=C)c(Br)c2Br)c(Br)c1Br]

Thus, FIG. 1 illustrates an example of a process of forming a vinyl-PBDE compound. The vinyl functional group enables covalent bonding to a material in which it is embedded, thereby mitigating "leach out" associated with existing polybrominated diphenyl-based flame retardant compounds, such as decabromodiphenyl ether and decabromodiphenyl ethane.

Figure 2A:
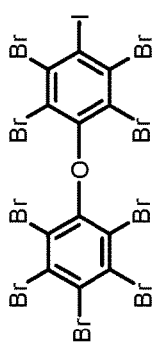
FIGS. 2A to 2D are chemical reaction diagrams illustrating processes for utilizing an iodo-polybrominated diphenyl ether (Iodo-PBDE) compound for further functionalization, according to various embodiments.
Figure 2A:
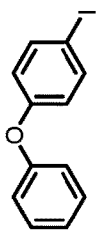
Figure 2B:
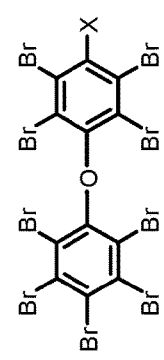
Figure 2B:
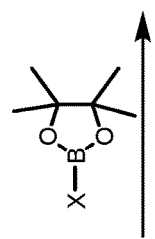
Figure 2B:
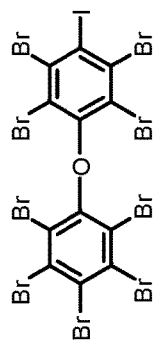
Figure 2C:
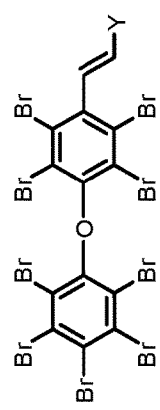
Figure 2C:
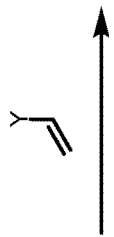
Figure 2C:
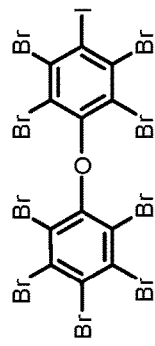
Figure 2D:
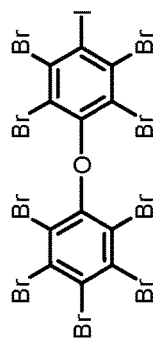
Figure 2D:
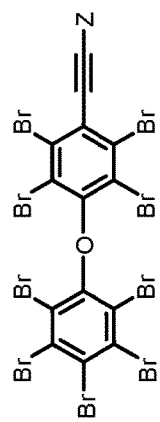

FIG. 2A is a chemical reaction diagram 200 illustrating an example of a process of forming an iodo-polybrominated diphenyl ether (Iodo-PBDE) compound, according to a particular embodiment. FIGS. 2B to 2D are chemical reaction diagrams 210, 220, 230 illustrating examples of processes of utilizing the Iodo-PBDE compound of FIG. 2A for Palladium-catalyzed cross-coupling reactions, according to various embodiments.

Referring to the chemical reaction diagram 200 of FIG. 2A, an iodo-functionalized diphenyl ether compound is utilized to form an iodo-PBDE compound. In the particular embodiment depicted in FIG. 2A, the iodo-functionalized diphenyl ether compound is 4-iodo-diphenyl ether (IUPAC name 1-iodo-4-phenoxybenzene). FIG. 2A illustrates that the 4-iodo-diphenyl ether compound is polybrominated using bromination methods similar to those described herein with respect to the second chemical reaction depicted in FIG. 1, resulting in an iodo-PBDE compound having the following structural formula:

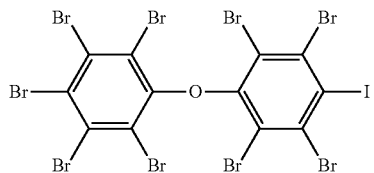 [SMILES: Brc1c(Br)c(Br)c(Oc2c(Br)c(Br)c(I)c(Br)c2Br)c(Br)c1Br]

It will be appreciated that the 4-iodo-diphenyl ether compound depicted in FIG. 2A is one example of an iodo-functionalized diphenyl ether compound and that the iodo group may be positioned at an alternative location on the phenyl ring. Examples of such alternative iodo-functionalized diphenyl ether compounds include 1-iodo-3-phenoxybenzene and 1-iodo-2-phenoxybenzene. Further, it will be appreciated that alternative iodo-functionalized diphenyl ether compounds containing iodo groups on both phenyl rings may be also utilized. An example of such an alternative iodo-functionalized diphenyl ether compound is 1,1'-Oxybis(4-iodobenzene).

In the case of the alternative starting material of 1,1'-Oxybis(4-iodobenzene), for a similar reaction scheme, an octa-brominated diphenyl ether compound with multiple iodo groups may be formed, having the following structural formula:

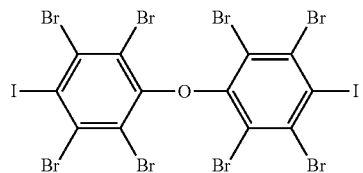 [SMILES: Brc1c(Br)c(Oc2c(Br)c(Br)c(I)c(Br)c2Br)c(Br)c(Br)c1I]

The chemical reaction diagram 210 of FIG. 2B illustrates a first example of a Palladium-catalyzed cross-coupling reaction that utilizes the iodo-PBDE compound of FIG. 2A. In the particular embodiment depicted in FIG. 2B, the Palladium-catalyzed cross-coupling reaction is a Suzuki cross-coupling reaction that utilizes a boronic ester. In the embodiment depicted in FIG. 2B, the boronic ester is a boronic acid pinacol ester having the following generic structural formula:

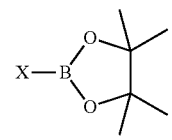

Examples of commercially available boronic acid pinacol esters include vinylboronic acid pinacol ester and allylboronic acid pinacol ester. The right side of the chemical reaction diagram 210 illustrates that the Suzuki cross-coupling reaction yields a functionalized PBDE compound having the following generic structural formula:

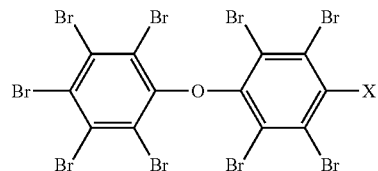

In the generic structural formula above, X may correspond to a vinyl group or an aryl group, in some embodiments. These groups can be further chosen from commercially available compounds that contain functionalities that can be used to react and bind into polymeric resin systems. These groups can include hydroxyls, amines, epoxides, vinyls, esters, carboxylic acids, acrylates, etc.

As a prophetic example, a suspension of the iodo-PBDE compound of FIG. 2A (1.0 equiv.), either vinyl boronic acid, a vinyl boronic ester (e.g., vinylboronic acid pinacol ester), or potassium trifluoroborate (1.25 equiv.), and a base such as Na₂CO₃, K₂CO₃, Cs₂CO₃, KOH in DMF may be sparged with argon for 10 minutes. Alternately, a solution of water and toluene with a trace amount of tetrabutylammonium bromide (TBAB) may be used instead of DMF. 1,1'-Bis(diphenylphosphino)ferrocene)palladium(II) dichloride (PdCl₂(dppf)) (2.5-10 mol %) may be added to the reaction mixture, which may be heated at 90° C. for 4-16 hours. The reaction mixture may be partitioned between ethyl acetate (EtOAc) and saturated aqueous NaHCO₃, washed with water, brine, dried over MgSO₄, and the solvents removed in vacuo. The residue may be purified by column chromatography on silica gel with EtOAc/hexanes as the eluent.

The chemical reaction diagram 220 of FIG. 2C illustrates a second example of a Palladium-catalyzed cross-coupling reaction that utilizes the iodo-PBDE compound of FIG. 2A. In the particular embodiment depicted in FIG. 2C, the Palladium-catalyzed cross-coupling reaction is a Heck cross-coupling reaction. The Y functionality may be limited to electron deficient groups, such as esters, carboxylic acids, and nitriles. However, after the Heck cross-coupling reaction, such electron deficient groups could be reduced to hydroxyl groups.

The right side of the chemical reaction diagram 220 illustrates that the Heck cross-coupling reaction yields a functionalized PBDE compound having the following generic structural formula:

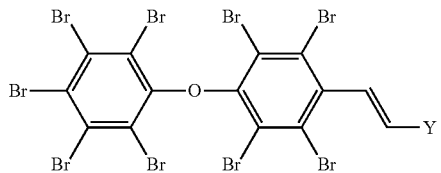

As a prophetic example, the iodo-PBDE compound of FIG. 2A (1 equiv.), "Group Y" (2 equiv.), TBAB (1 equiv.), a base such as Na₂CO₃, Cs₂CO₃, KOH (3 equiv.), and PdCl₂ (2 mol %) may be dissolved with DMF or water/toluene (1:1). The reaction mixture may be sonicated at ambient temperature (25° C.) in running water bath for 6 hours or heated at reflux for 24 hours. The reaction mixture may be extracted with ethyl acetate. The combined organic extracts may be dried over anhydrous Na₂SO₄ and the solvents removed in vacuo. The crude mixture may be purified by column chromatography over silica gel.

The chemical reaction diagram 230 of FIG. 2D illustrates a third example of a Palladium-catalyzed cross-coupling reaction that utilizes the iodo-PBDE compound of FIG. 2A. In the particular embodiment depicted in FIG. 2D, the Palladium-catalyzed cross-coupling reaction is a Sonogashira cross-coupling reaction.

The right side of the chemical reaction diagram 230 illustrates that the Sonogashira conditions yield a functionalized PBDE compound having the following generic structural formula:

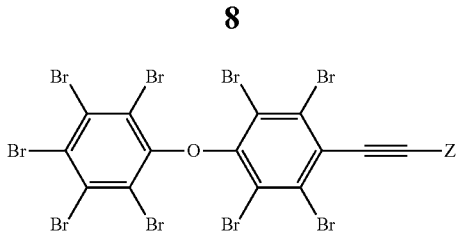

In the generic structural formula above, Z may correspond to a vinyl group or an aryl group, in some embodiments. These groups can be further chosen from commercially available compounds that contain functionalities that can be used to react and bind into polymeric resin systems. These groups can include hydroxyls, amines, epoxides, vinyls, ester, carboxylic acids, acrylates, etc.

As a prophetic example, a solution of the iodo-PBDE compound of FIG. 2A, triethylamine (NEt₃), the alkyne, CuI in anhydrous benzene may be sparged with argon. After 10-15 minutes, Pd(PPh₃)₂Cl₂ and PPh₃ may be added, and the mixture sparged with argon and stirred at ambient temperature until the reaction is complete. The solvent may be removed under reduced pressure, the residue dried in air, and the products isolated by extraction into hexane or petroleum ether. In some cases, the product may be additionally purified by flash chromatography on silica gel using hexane-ethyl acetate (20:1) as eluent.

Thus, FIGS. 2A to 2D illustrate an example of a process of forming an iodo-PBDE compound and utilizing the Iodo-PBDE compound for various Palladium-catalyzed cross-coupling reactions. The iodo functional group enables covalent bonding to a material in which it is embedded, thereby mitigating "leach out" associated with existing polybrominated diphenyl-based flame retardant compounds, such as decabromodiphenyl ether and decabromodiphenyl ethane.

FIGS. 3A to 3D are chemical reaction diagrams 300, 310, 320, 330 illustrating examples of processes of utilizing a hydroxyl-polybrominated diphenyl ether (Hydroxyl-PBDE) compound for further functionalization, according to various embodiments.

Figure 3A:
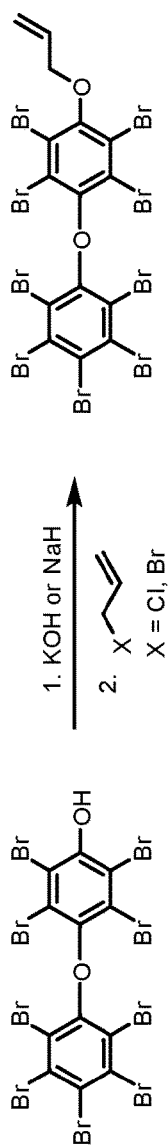
FIGS. 3A to 3D are chemical reaction diagrams illustrating processes for utilizing a hydroxyl-polybrominated diphenyl ether (Hydroxyl-PBDE) compound for further functionalization, according to various embodiments.

In FIG. 3A, a hydroxy-functionalized PBDE compound is utilized to form an allyl-PBDE compound. In the particular embodiment depicted in FIG. 3A, the hydroxy-functionalized PBDE compound is 4'-hydroxy-2,2', 3,3', 4,4', 5,5', 6,6' nonabromodiphenyl ether (aka 4-Phenoxyphenol), having the following structural formula:

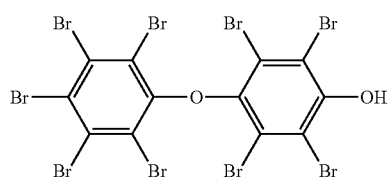

The chemical reaction diagram 300 of FIG. 3A illustrates that the hydroxy-PBDE compound may be reacted via nucleophilic substitution chemistry to yield an allyl-PBDE compound having the following structural formula:

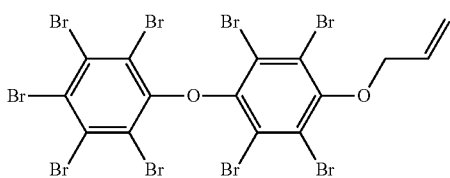

As a prophetic example, the hydroxy-PBDE compound may be added to a solution of KOH or NaH dissolved in anhydrous THF, 1,4-dioxane, acetone, or DMF for reaction via nucleophilic substitution chemistry with an allyl chloride (where X=Cl) or an allyl bromide (where X=Br), yielding the allyl-PBDE compound. After stirring for 30 minutes, the allyl halide may be added dropwise at or below ambient temperature and the reaction may be stirred for several hours. The reaction mixture may be extracted with ethyl acetate, benzene, or toluene. The combined organic extracts may be dried over anhydrous $Na_2SO_4$ and the solvents removed in vacuo. The crude mixture may be purified by column chromatography over silica gel.

It will be appreciated that the 4'-hydroxy-2,2', 3,3', 4,4', 5,5', 6,6' nonabromodiphenyl ether compound depicted in FIG. 3A is one example of a hydroxy-PBDE compound and that the hydroxyl group may be positioned at an alternative location on the phenyl ring. As a first example, 3-Phenoxyphenol may be utilized to form 3'-hydroxy-2,2', 3,3', 4,4', 5,5', 6,6' nonabromodiphenyl ether. As a second example, 2-Phenoxyphenol may be utilized to form 2'-hydroxy-2,2', 3,3', 4,4', 5,5', 6,6' nonabromodiphenyl ether. Further, it will further be appreciated that alternative hydroxy-PBDE compounds containing hydroxyl groups on both phenyl rings may be also utilized. Examples of alternative hydroxy-PBDE compounds include 4,4'-Dihydroxydiphenyl ether and 2,2'-Dihydroxydiphenyl ether.

In the case of the alternative starting material of 4,4'-Dihydroxydiphenyl ether, for a similar reaction scheme, an octa-brominated diphenyl ether compound with multiple allyl groups may be formed, having the following structural formula:

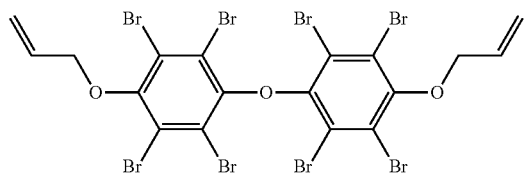 [SMILES: C=CCOc1c(Br)c(Br)c(Oc2c(Br)c(Br)c(OCC=C)c(Br)c2Br)c(Br)c1Br]

Figure 3B:
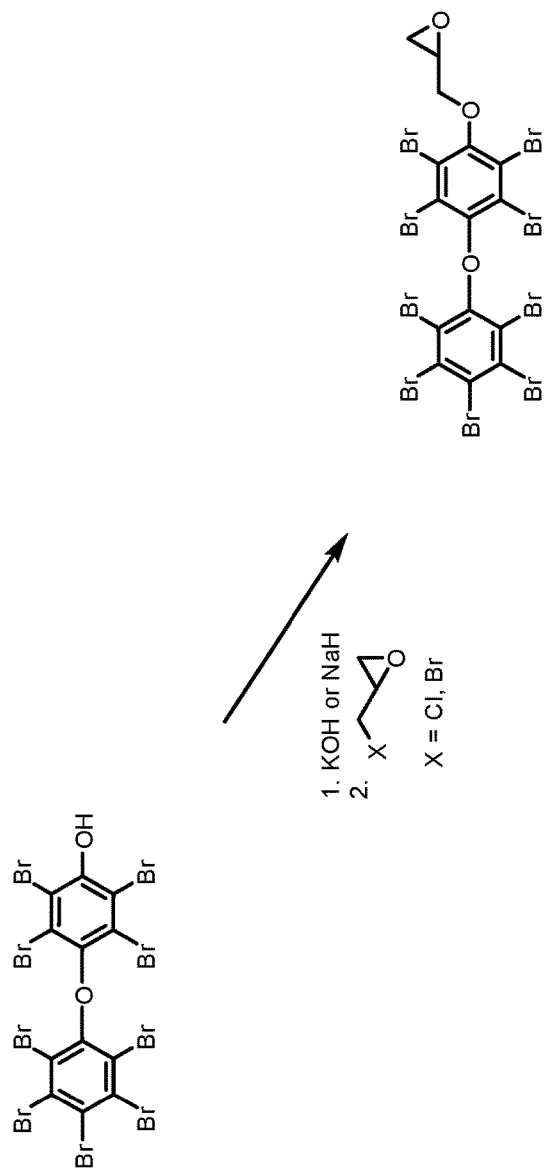

The chemical reaction diagram 310 of FIG. 3B illustrates that the hydroxy-PBDE compound may be reacted via nucleophilic substitution chemistry to yield an epoxy-PBDE compound having the following structural formula:

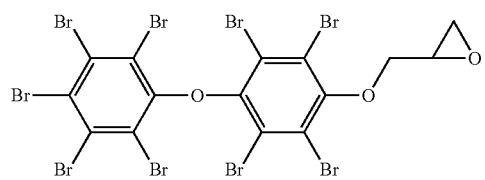 [SMILES: Brc1c(Br)c(Br)c(Oc2c(Br)c(Br)c(OCC3CO3)c(Br)c2Br)c(Br)c1Br]

As a prophetic example, the hydroxy-PBDE compound may be added to a solution of KOH or NaH dissolved in anhydrous THF, 1,4-dioxane, acetone, or DMF for reaction via nucleophilic substitution chemistry with an epoxy chloride (where X=Cl) or an epoxy bromide (where X=Br), yielding the epoxy-PBDE compound. After stirring for 30 minutes, the allyl halide may be added dropwise at or below ambient temperature and the reaction may be stirred for several hours. The reaction mixture may be extracted with ethyl acetate, benzene, or toluene. The combined organic extracts may be dried over anhydrous $Na_2SO_4$ and the solvents removed in vacuo. The crude mixture may be purified by column chromatography over silica gel.

In the case of the alternative starting material of 4,4'-Dihydroxydiphenyl ether, for a similar reaction scheme, an octa-brominated diphenyl ether compound with multiple epoxy groups may be formed, having the following structural formula:

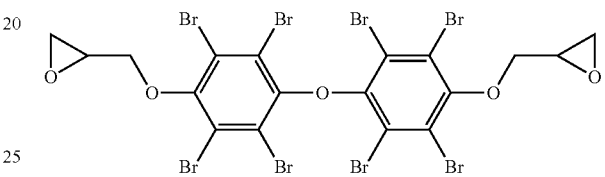

Figure 3C:
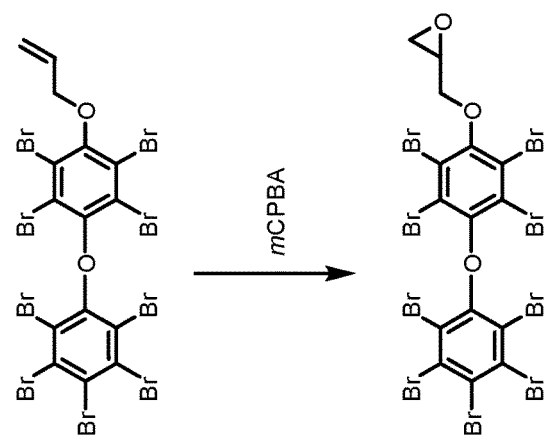

The chemical reaction diagram 320 of FIG. 3C illustrates an alternative method of forming the epoxy-PBDE compound of FIG. 3B by reacting the allyl-PBDE compound of FIG. 3A with mCPBA.

Figure 3D:
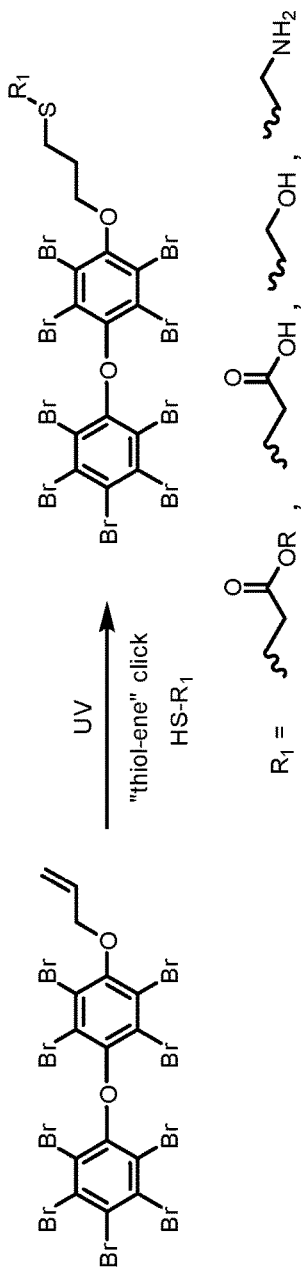

The chemical reaction diagram 330 of FIG. 3D illustrates that the allyl-PBDE compound of FIG. 3A can be reacted via "thiol-ene" click chemistry with thiol compounds (HS-$R_1$) where $R_1$ may represent a functional group such as an ester group, a carboxylic acid group, a hydroxyl group, or an amine group (among other alternatives). The right side of FIG. 3D illustrates a functionalized PBDE compound having the following generic structural formula:

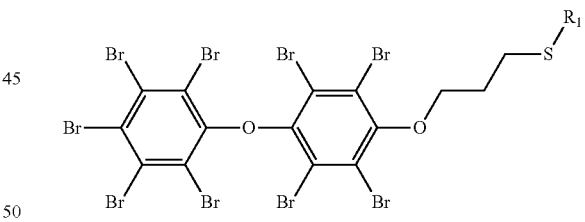

As a prophetic example, the allyl-PBDE compound of FIG. 3A (1.0 eq.) and thiol compound (i.e., cysteamine hydrochloride, 3-mercaptopropioinc acid, and mercaptoethanol; 6.0 eq.) may be dissolved in a minimum of methanol, ethanol, DMSO, or DMF. The solution may be irradiated in a UV reactor. The reactions may be monitored by $^1$H NMR. Upon completion of the reaction, the resulting mixture may be dissolved in water, and $K_2CO_3$ may be added to reach a pH of 9. The solution may then be extracted with ethyl acetate, dried over $Na_2SO_4$ and the solvent removed in vacuo.

Utilizing an octa-brominated diphenyl ether compound with multiple allyl groups may yield an octa-brominated diphenyl ether compound with multiple functional groups having the generic structural formula:

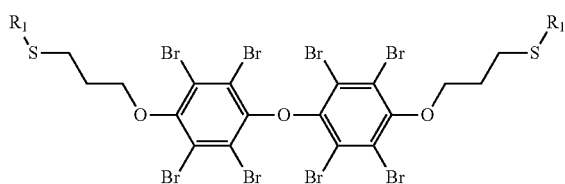

Thus, FIGS. 3A to 3D illustrate an example of a process of utilizing a Hydroxyl-PBDE compound for functionalization with various functional groups. The various functional groups enables covalent bonding to a material in which it is embedded, thereby mitigating "leach out" associated with existing polybrominated diphenyl-based flame retardant compounds, such as decabromodiphenyl ether and decabromodiphenyl ethane.

Figure 4A:
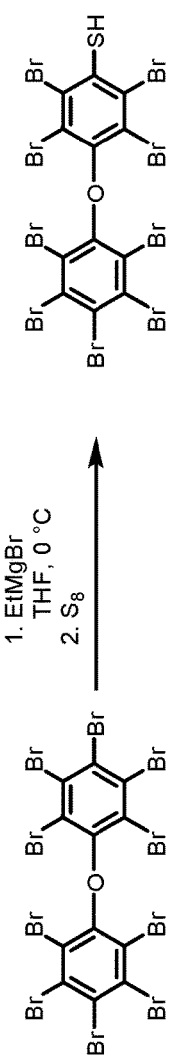
FIGS. 4A to 4D are chemical reaction diagrams illustrating processes for utilizing a thiol-polybrominated diphenyl ether (Thiol-PBDE) compound for further functionalization, according to various embodiments.
Figure 4B:
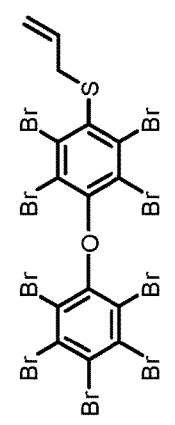
Figure 4B:
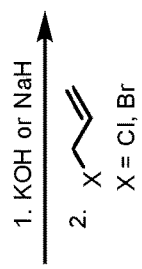
Figure 4B:
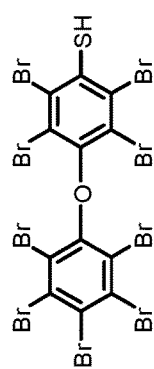
Figure 4C:
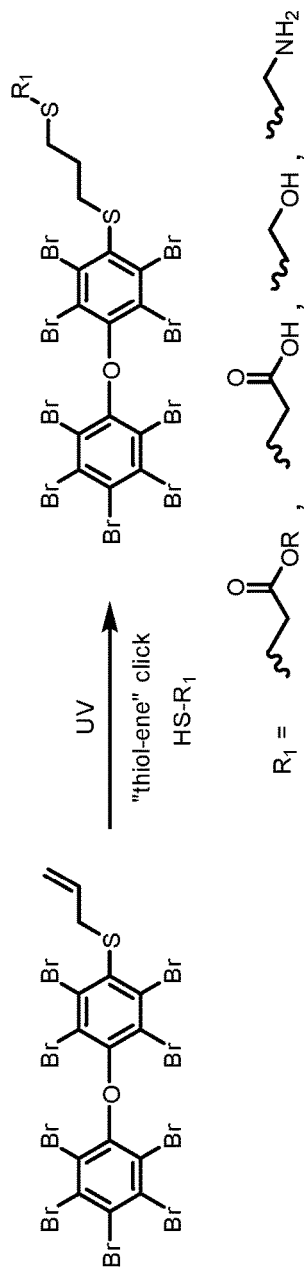
Figure 4D:
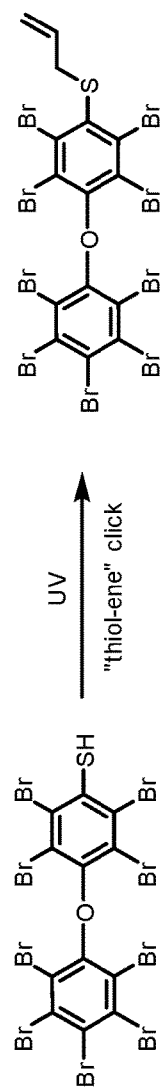

FIG. 4A is a chemical reaction diagram 400 illustrating an example of a process of forming a thiol-polybrominated diphenyl ether (Thiol-PBDE) compound, according to a particular embodiment. FIGS. 4B to 4D are chemical reaction diagrams 410, 420, 430 illustrating examples of processes of utilizing the Thiol-PBDE compound of FIG. 4A for further functionalization, according various embodiments.

Referring to the chemical reaction diagram 400 of FIG. 4A, DBDPE is utilized to form a Thiol-PBDE compound via Grignard chemistry. DBDPE may be reacted with ethylmagnesium bromide and quenched with sulfur to give a thiol-PBDE compound having the following structural formula:

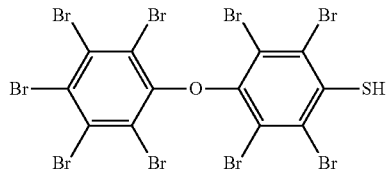

In some cases, the thiol group of the Thiol-PBDE compound may be reacted to polymeric resin systems or further functionalized, as described further herein with respect to FIGS. 4B to 4D.

As a prophetic example, ethylmagnesium bromide (EtMgBr) may be reacted with DBDPE in a tetrahydrofuran (THF) solvent at a temperature of 0° C. for Grignard reagent formation (identified as step 1 in FIG. 4A), followed by reaction with sulfur ($S_8$), identified as step 2 in FIG. 4A, to form the thiol-PBDE compound.

The chemical reaction diagram 410 of FIG. 4B illustrates that the Thiol-PBDE compound of FIG. 4A may be reacted via nucleophilic substitution chemistry to yield an Allyl-PBDE compound having the following structural formula:

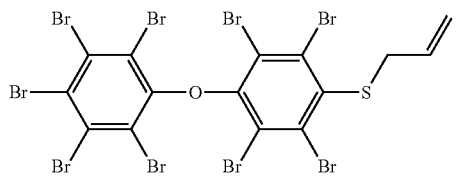 [SMILES: C=CCSc1c(Br)c(Br)c(Oc2c(Br)c(Br)c(Br)c(Br)c2Br)c(Br)c1Br]

In a particular embodiment, the Allyl-PBDE compound of FIG. 4B may be formed using nucleophilic substitution chemistry similar to that previously described herein with respect to FIG. 3A.

The chemical reaction diagram 420 of FIG. 4C illustrates that the Allyl-PBDE compound of FIG. 4B can be reacted via "thiol-ene" click chemistry with thiol compounds (HS-$R_1$) where $R_1$ may represent a functional group such as an ester group, a carboxylic acid group, a hydroxyl group, or an amine group (among other alternatives). The right side of FIG. 4C illustrates a functionalized PBDE compound having the following generic structural formula:

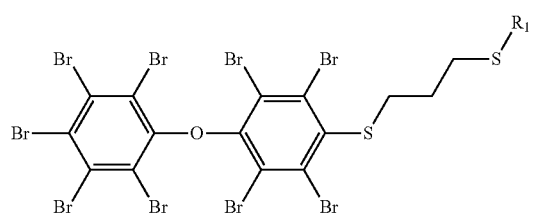

In a particular embodiment, the functionalized PBDE compound of FIG. 4C may be formed using "thiol-ene" click chemistry similar to that previously described herein with respect to FIG. 3D.

The chemical reaction diagram 430 of FIG. 4D illustrates an alternative method of forming the Allyl-PBDE compound of FIG. 4B by reacting the Thiol-PBDE compound of FIG. 4A with alkene systems via "thiol-ene" chemistry.

As a prophetic example, the Thiol-PBDE compound of FIG. 4A and an allyl chloride or an allyl bromide may be dissolved in a minimum of methanol, ethanol, DMSO, or DMF. The solution may be irradiated in a UV reactor. The reactions may be monitored by $^1$H NMR. Upon completion of the reaction, the resulting mixture may be dissolved in water, and $K_2CO_3$ may be added to reach pH of 9. The solution was then extracted with ethyl acetate, dried over $Na_2SO_4$ and the solvent removed in vacuo.

Thus, FIGS. 4A to 4D illustrate an example of a process of forming a Thiol-PBDE compound and utilizing the Thiol-PBDE compound for functionalization with various functional groups. The various functional groups enable covalent bonding to a material in which it is embedded, thereby mitigating "leach out" associated with existing polybrominated diphenyl-based flame retardant compounds, such as decabromodiphenyl ether and decabromodiphenyl ethane.

Figure 5A:
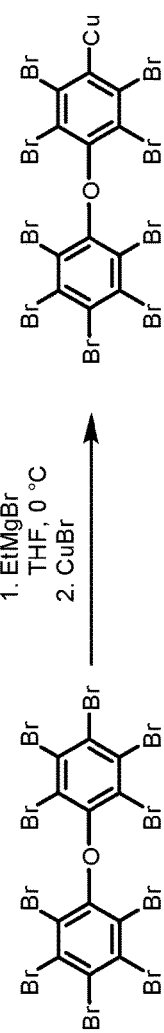
FIGS. 5A to 5F are chemical reaction diagrams illustrating processes for forming an organocuprate compound from a PBDE compound and utilizing the organocuprate compound for further functionalization, according to various embodiments.

FIG. 5A is a chemical reaction diagram 500 illustrating that the Grignard generated from the reaction of decabromodiphenyl ether and ethylmagnesium bromide, as shown in FIG. 4A, may be transformed into an organocuprate compound. FIGS. 5B to 5F are chemical reaction diagrams 510-550 illustrating examples of processes for utilizing the organocuprate compound of FIG. 5A for further functionalization, according various embodiments.

Referring to the chemical reaction diagram 500 of FIG. 5A, DBDPE is utilized to form an organocuprate compound via transmetallation with copper (I) bromide, with the resulting organocuprate compound identified subsequently as "$C_{12}Br_9CuO$" having the structural formula:

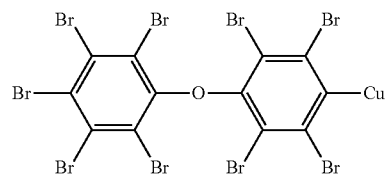

As a prophetic example, ethylmagnesium bromide (EtMgBr; 1.05 equiv.) may be reacted with DBDPE (1.0 equiv.) in a tetrahydrofuran (THF) solvent at a temperature of 0° C. for Grignard reagent formation (step 1 in FIG. 5A), followed by a transmetallation reaction with CuBr via rapid addition of anhydrous cuprous bromide (1.30 equiv.). The mixture may be stirred at this temperature for 2 hours, resulting in the formation of the organocuprate compound.

Figure 5B:
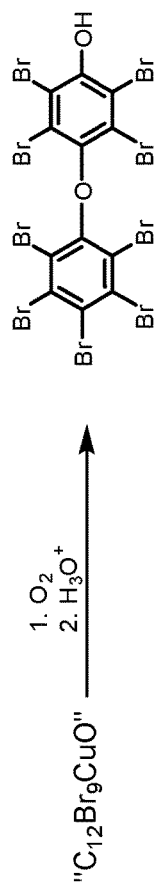

The chemical reaction diagram 510 of FIG. 5B illustrates that reacting the organocuprate compound of FIG. 5A with oxygen yields the hydroxy-functionalized PBDE compound depicted in FIG. 3A.

As a prophetic example, a solution of the organocuprate reagent may be oxidized with dry oxygen for 2 hours, and may be hydrolyzed with HCl. The reaction mixture may be extracted with benzene, rinsed with water and brine, dried over $Na_2SO_4$ and the solvents removed in vacuo. Purification may be performed by extracting the crude solid with hot dilute (10%) NaOH solution followed by acidification of the basic solution to yield a precipitate. The precipitate may be purified further by recrystallization from benzene or toluene.

Figure 5C:
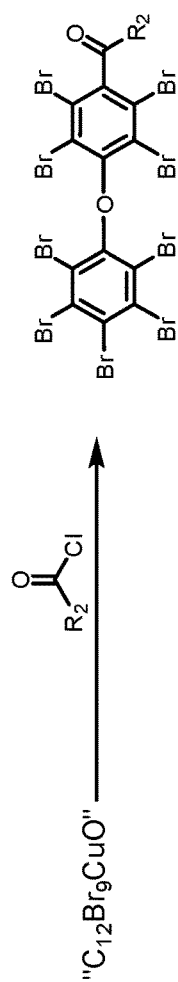

The chemical reaction diagram 520 of FIG. 5C illustrates that reacting the organocuprate compound of FIG. 5A with an acid chloride yields a PBDE ketone having the following structural formula:

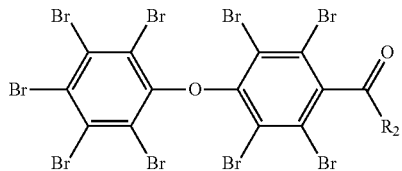

In the above formula, $R_2$ may correspond to an alkyl or aryl group. Illustrative, non-limiting example of alkyl groups include a methyl group or an ethyl group, up to a C12 or C16 alkyl chain (including branching, in some cases). Illustrative, non-limiting examples of aryl groups include a phenyl group, a tolyl group, or a naphthyl group. In a particular embodiment, the acid chloride includes benzoyl chloride.

As a prophetic example, benzoyl chloride (1.4 equiv.) may be added rapidly to a THF solution of the organocuprate compound of FIG. 5A (1.0 equiv.) at 0° C. The reaction mixture may be stirred for 1 hour at this temperature, followed by gradual warming to ambient temperature. After 22 hours, the reaction mixture may be hydrolyzed with 6 N HCl. The reaction mixture may be extracted with benzene, rinsed with water and brine, dried over $Na_2SO_4$ and the solvents removed in vacuo. The crude solid may be washed with acetone (4×), and the acetone washings concentrated to a thick gum. Purification may include sublimation of the gum, stirring in solution over activated charcoal, hot filtration, and recrystallization.

Figure 5D:
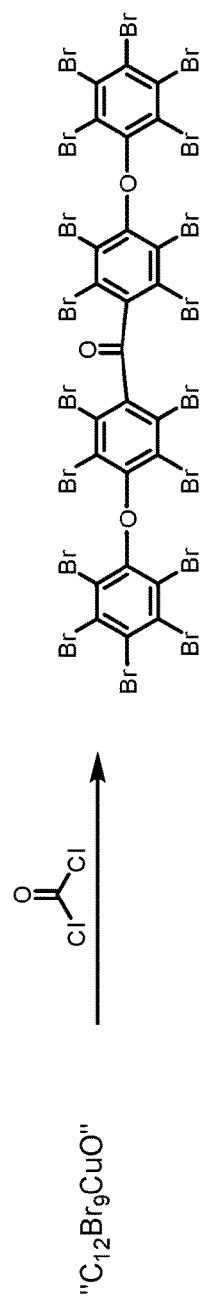

The chemical reaction diagram 530 of FIG. 5D illustrates that reacting the organocuprate compound of FIG. 5A with phosgene yields a bisPBDE ketone having the following structural formula:

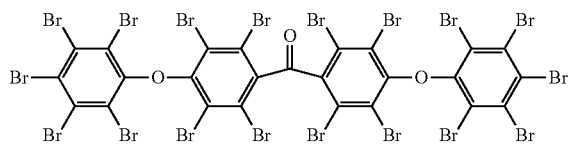

As a prophetic example, phosgene (0.4 equiv.) may be added rapidly to a THF solution of the organocuprate compound of FIG. 5A (1.0 equiv.) at 0° C. The reaction mixture may be stirred for 1 hour at this temperature, followed by gradual warming to ambient temperature. After 22 hours, the reaction mixture may be hydrolyzed with HCl. The reaction mixture may be extracted with benzene, rinsed with water and brine, dried over $Na_2SO_4$ and the solvents removed in vacuo. The crude solid may be washed with acetone (4×), and the acetone washings concentrated to a thick gum. Purification may include sublimation of the gum, stirring in solution over activated charcoal, hot filtration, and recrystallization.

In some embodiments, the bisPBDE ketone of FIG. 5D may be utilized for cross-linking with polyether ether ketone (PEEK), among other alternatives.

Figure 5E:
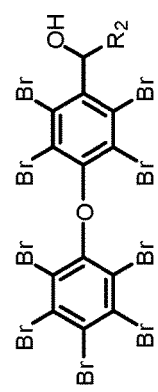
Figure 5E:
Figure 5E:
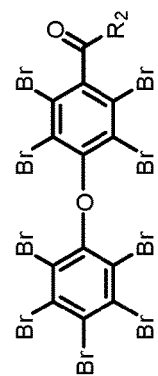

The chemical reaction diagram 540 of FIG. 5E illustrates that the PBDE ketone of FIG. 5C can be reduced to a hydroxyl-PBDE compound having the following structural formula:

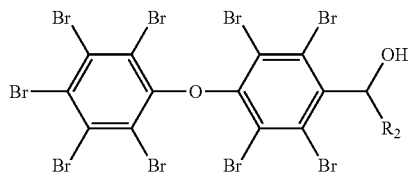

The hydroxyl-PBDE compound of FIG. 5E may be used in resin systems as-is, or the hydroxyl-PBDE compound of FIG. 5E may be reacted in a similar fashion as in FIGS. 3A-3D to add additional functionality, as illustrated and further described herein with respect to FIGS. 6A to 6D.

As a prophetic example, to a stirred suspension of $NaBH_4$ (4 equiv.) in 500 mL of anhydrous THF at 0° C. was added a solution of the PBDE ketone of FIG. 5C (1 equiv.) in 50 mL of anhydrous THF, dropwise. The reaction mixture may be stirred for 4 hours and quenched by the dropwise addition of 2N HCl. The solids may be removed by filtration and the layers of the filtrate separated. The aqueous layer may be rinsed with diethyl ether (×3), and the combined organic layers rinsed with $NaHCO_3$, brine, and dried over $MgSO_4$. The solvent may be removed in vacuo, and the resulting crude product may be purified by vacuum distillation or other techniques known by those skilled in the art.

Figure 5F:
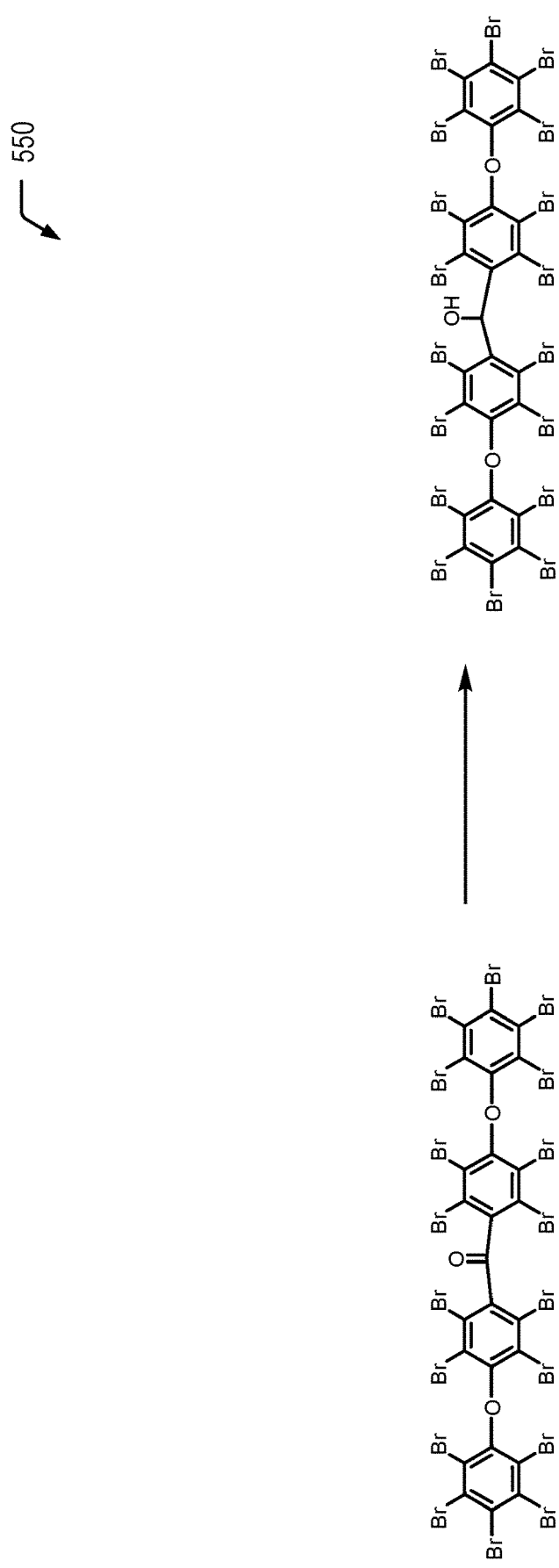

The chemical reaction diagram 550 of FIG. 5F illustrates that the bisPBDE ketone of FIG. 5D can be reduced to a hydroxyl-PBDE compound having the following structural formula:

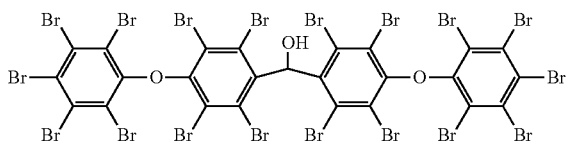

The hydroxyl-PBDE compound of FIG. 5F may be used in resin systems as-is, or the hydroxyl-PBDE compound of FIG. 5F may be reacted in a similar fashion as in FIGS. 3A-3D to add additional functionality, as illustrated and further described herein with respect to FIGS. 7A to 7D. In a particular embodiment, the hydroxyl-PBDE compound of FIG. 5F may be formed in a similar manner to that previously described herein with respect to FIG. 5E.

Thus, FIGS. 5A to 5F illustrate an example of a process of forming an organocuprate compound and utilizing the organocuprate compound for functionalization with various functional groups. The various functional groups enable covalent bonding to a material in which it is embedded, thereby mitigating "leach out" associated with existing polybrominated diphenyl-based flame retardant compounds, such as decabromodiphenyl ether and decabromodiphenyl ethane.

FIGS. 6A to 6D are chemical reaction diagrams 600, 610, 620, 630 illustrating examples of processes of utilizing the hydroxyl-PBDE compound of FIG. 5E for further functionalization, according to various embodiments.

Figure 6A:
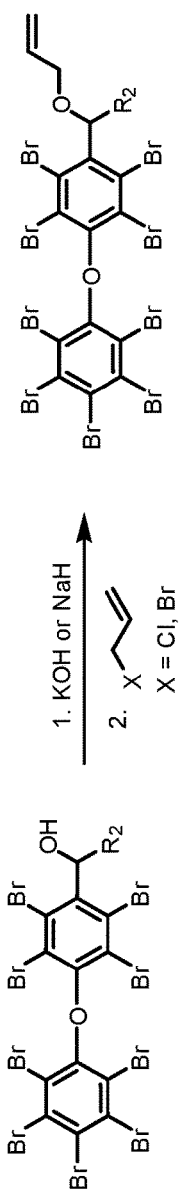
FIGS. 6A to 6D are chemical reaction diagrams illustrating processes for utilizing the Hydroxyl-PBDE compound of FIG. 5E for further functionalization, according to various embodiments.

The chemical reaction diagram 600 of FIG. 6A illustrates that the hydroxy-PBDE compound of FIG. 5E may be reacted via nucleophilic substitution chemistry to yield an allyl-PBDE compound having the following structural formula:

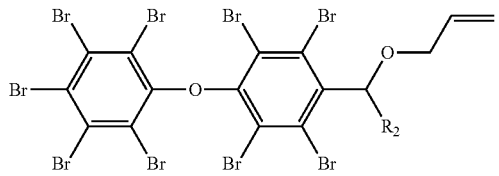

In a particular embodiment, the Allyl-PBDE compound of FIG. 6A may be formed in a similar manner to that previously described herein with respect to FIG. 3A.

Figure 6B:
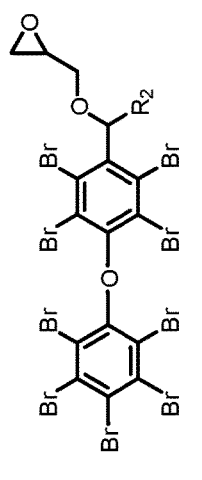
Figure 6B:
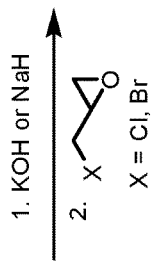
Figure 6B:
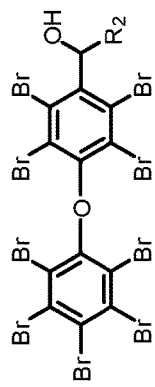

The chemical reaction diagram 610 of FIG. 6B illustrates that the hydroxy-PBDE compound of FIG. 5E may be reacted via nucleophilic substitution chemistry to yield an epoxy-PBDE compound having the following structural formula:

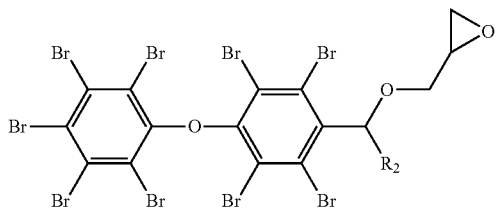

In a particular embodiment, the Epoxy-PBDE compound of FIG. 6B may be formed in a similar manner to that previously described herein with respect to FIG. 3B.

Figure 6C:
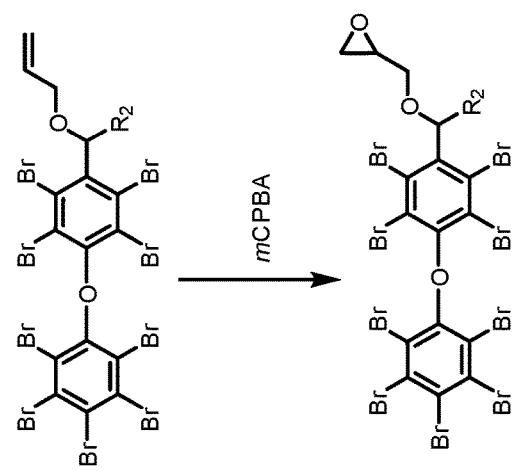

The chemical reaction diagram 620 of FIG. 6C illustrates an alternative method of forming the epoxy-PBDE compound of FIG. 6B by reacting the allyl-PBDE compound of FIG. 6A with mCPBA. In a particular embodiment, the epoxy-PBDE compound may be formed in a similar manner to that previously described herein with respect to FIG. 3C.

Figure 6D:
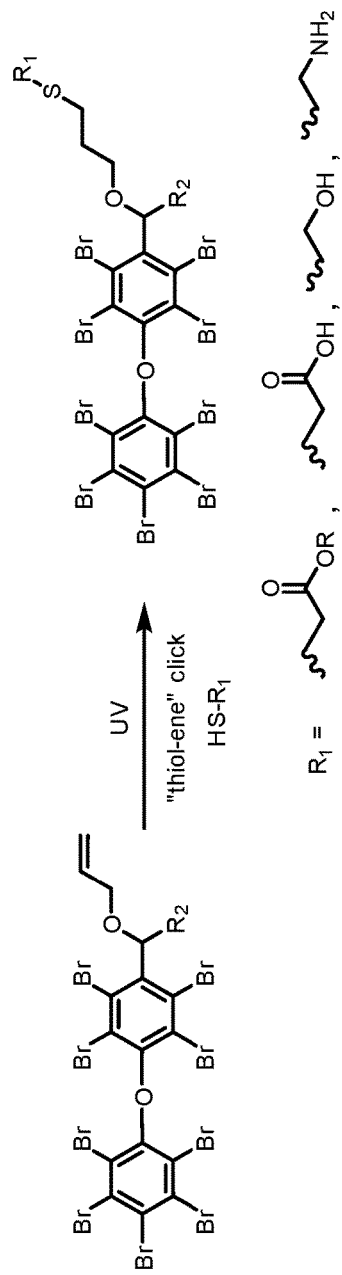

The chemical reaction diagram 630 of FIG. 6D illustrates that the allyl-PBDE compound of FIG. 6A can be reacted via "thiol-ene" click chemistry with thiol compounds (HS-R$_1$) where R$_1$ may represent a functional group such as an ester group, a carboxylic acid group, a hydroxyl group, or an amine group (among other alternatives). The right side of FIG. 6D illustrates a functionalized PBDE compound having the following generic structural formula:

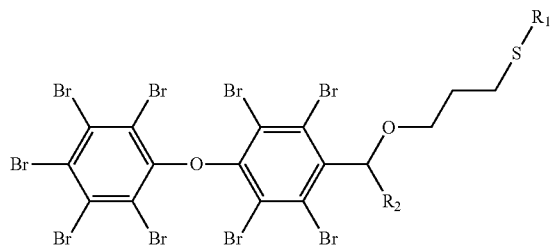

In a particular embodiment, the functionalized PBDE compound of FIG. 6D may be formed using "thiol-ene" click chemistry similar to that previously described herein with respect to FIG. 3D.

Thus, FIGS. 6A to 6D illustrate an example of a process of utilizing a Hydroxyl-PBDE compound for functionalization with various functional groups. The various functional groups enables covalent bonding to a material in which it is embedded, thereby mitigating "leach out" associated with existing polybrominated diphenyl-based flame retardant compounds, such as decabromodiphenyl ether and decabromodiphenyl ethane.

FIGS. 7A to 7D are chemical reaction diagrams 700, 710, 720, 730 illustrating examples of processes of utilizing the hydroxyl-PBDE compound of FIG. 5F for further functionalization, according to various embodiments.

Figure 7A:
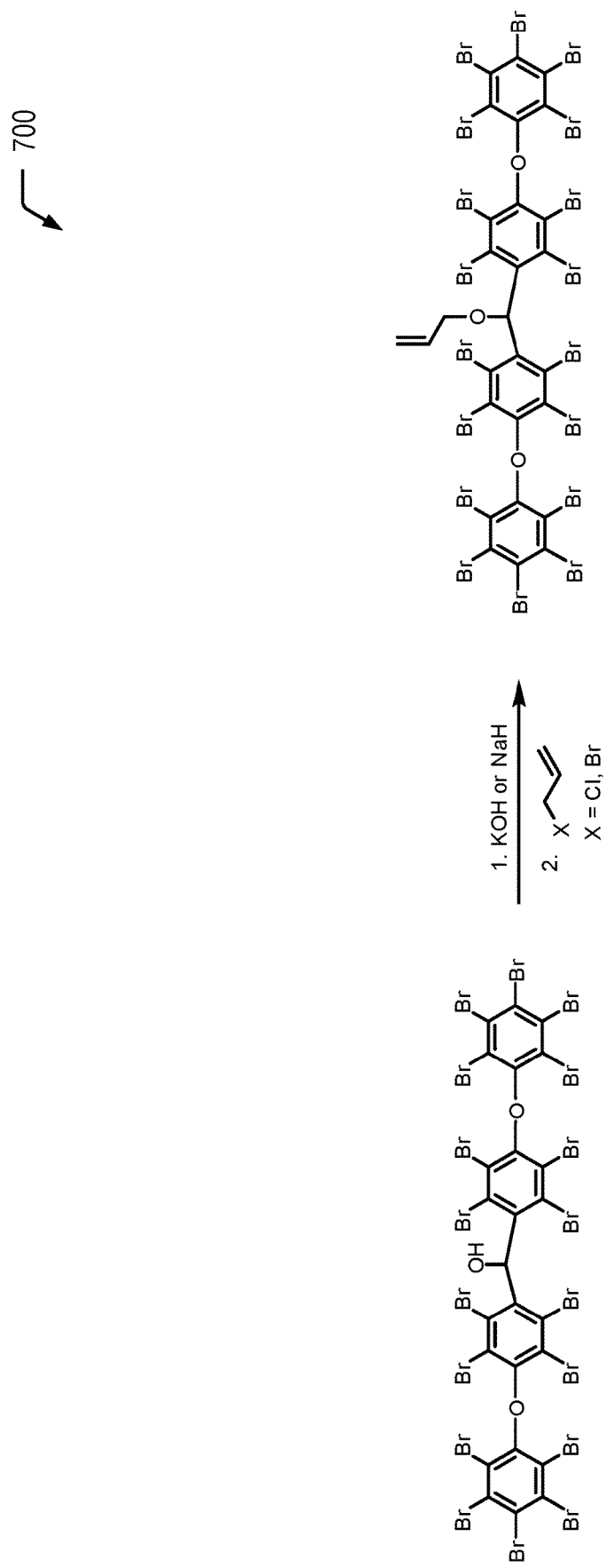
FIGS. 7A to 7D are chemical reaction diagrams illustrating processes for utilizing the Hydroxyl-PBDE compound of FIG. 5F for further functionalization, according to various embodiments.

The chemical reaction diagram 700 of FIG. 7A illustrates that the hydroxy-PBDE compound of FIG. 5F may be reacted via nucleophilic substitution chemistry to yield an allyl-PBDE compound having the following structural formula:

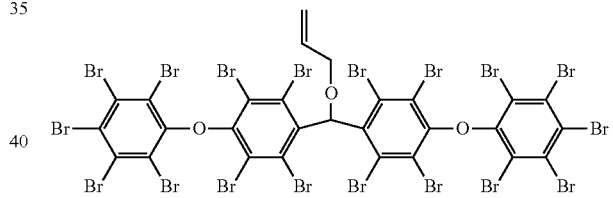

In a particular embodiment, the Allyl-PBDE compound of FIG. 7A may be formed in a similar manner to that previously described herein with respect to FIG. 3A.

Figure 7B:
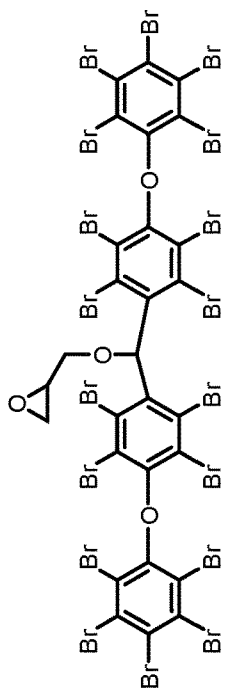
Figure 7B:
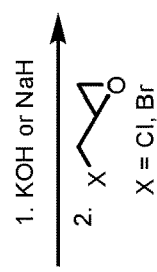
Figure 7B:
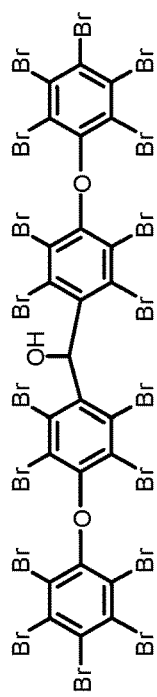

The chemical reaction diagram 710 of FIG. 7B illustrates that the hydroxy-PBDE compound of FIG. 5F may be reacted via nucleophilic substitution chemistry to yield an epoxy-PBDE compound having the following structural formula:

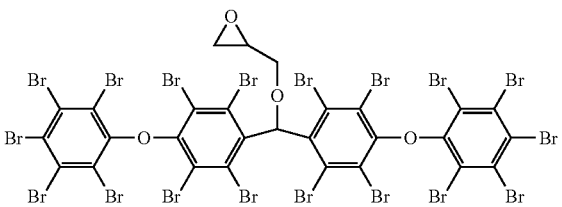 [SMILES: Brc1c(Br)c(Br)c(Oc2c(Br)c(Br)c(C(OCC3CO3)c3c(Br)c(Br)c(Oc4c(Br)c(Br)c(Br)c(Br)c4Br)c(Br)c3Br)c(Br)c2Br)c(Br)c1Br]

In a particular embodiment, the Epoxy-PBDE compound of FIG. 7B may be formed in a similar manner to that previously described herein with respect to FIG. 3B.

Figure 7C:
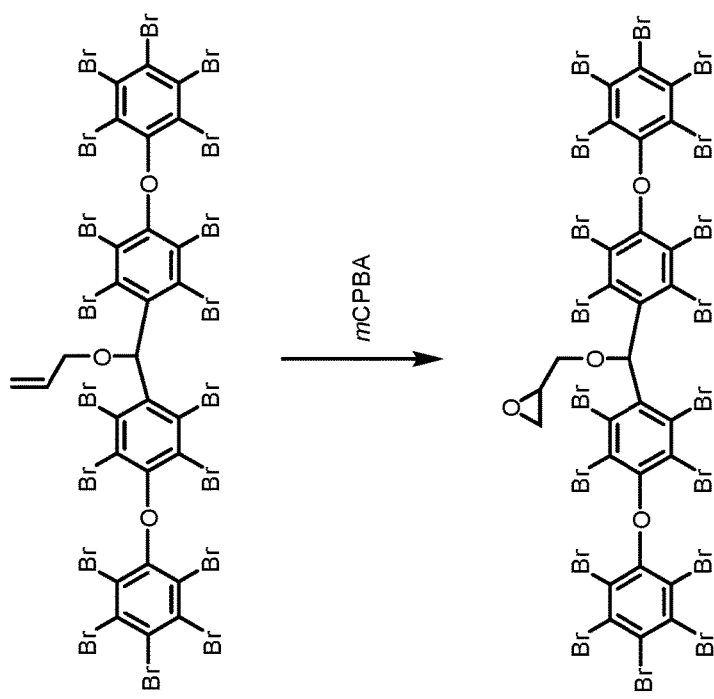

The chemical reaction diagram 720 of FIG. 7C illustrates an alternative method of forming the epoxy-PBDE compound of FIG. 7B by reacting the allyl-PBDE compound of FIG. 7A with mCPBA. In a particular embodiment, the epoxy-PBDE compound may be formed in a similar manner to that previously described herein with respect to FIG. 3C.

Figure 7D:
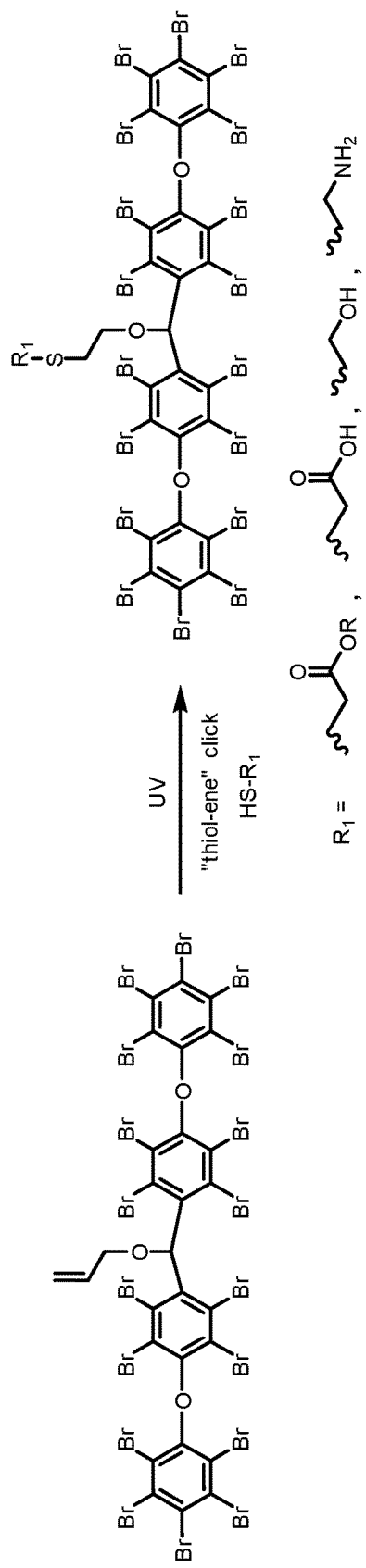

The chemical reaction diagram 730 of FIG. 7D illustrates that the allyl-PBDE compound of FIG. 7A can be reacted via "thiol-ene" click chemistry with thiol compounds (HS-R₁) where R₁ may represent a functional group such as an ester group, a carboxylic acid group, a hydroxyl group, or an amine group (among other alternatives). The right side of FIG. 7D illustrates a functionalized PBDE compound having the following generic structural formula:

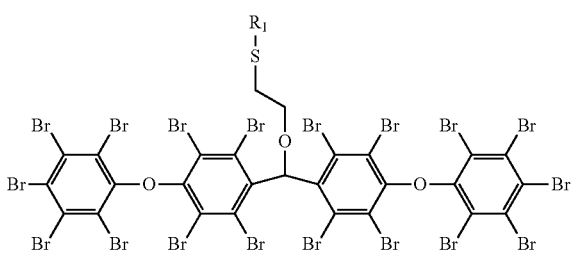

In a particular embodiment, the functionalized PBDE compound of FIG. 7D may be formed using "thiol-ene" click chemistry similar to that previously described herein with respect to FIG. 3D.

Thus, FIGS. 7A to 7D illustrate an example of a process of utilizing a Hydroxyl-PBDE compound for functionalization with various functional groups. The various functional groups enables covalent bonding to a material in which it is embedded, thereby mitigating "leach out" associated with existing polybrominated diphenyl-based flame retardant compounds, such as decabromodiphenyl ether and decabromodiphenyl ethane.

Figure 8A:
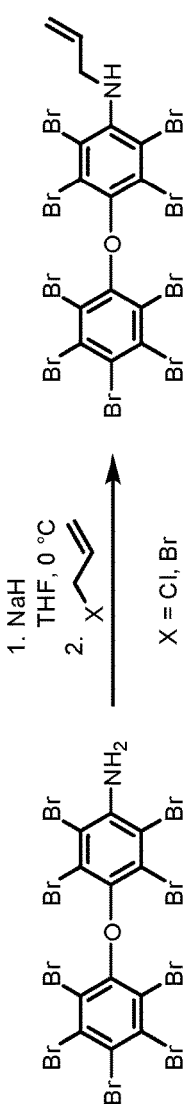
FIG. 8A is a chemical reaction diagram illustrating a process for functionalizing an amino-polybrominated diphenyl ether (Amino-PBDE) compound with an allyl group, according to a particular embodiment.
Figure 8B:
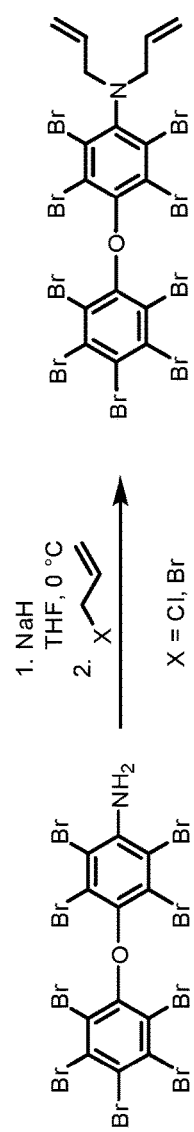
FIG. 8B is a chemical reaction diagram illustrating a process for functionalizing an amino-polybrominated diphenyl ether (Amino-PBDE) compound with multiple allyl groups, according to a particular embodiment.

FIGS. 8A and 8B are chemical reaction diagrams 800, 810 illustrating examples of processes of utilizing an amino-polybrominated diphenyl ether (Amino-PBDE) compound for further functionalization, according various embodiments.

In FIG. 8A, an amino-functionalized PBDE compound is utilized to form an allyl-PBDE compound. In the particular embodiment depicted in FIG. 8A, the amino-functionalized PBDE compound is 4'-amino-2,2', 3,3', 4,4', 5,5', 6,6' nonabromodiphenyl ether, having the following structural formula:

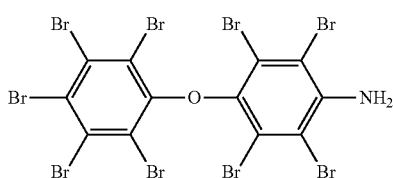 [SMILES: Nc1c(Br)c(Br)c(Oc2c(Br)c(Br)c(Br)c(Br)c2Br)c(Br)c1Br]

It will be appreciated that the 4'-amino-2,2', 3,3', 4,4', 5,5', 6,6' nonabromodiphenyl ether compound depicted in FIG. 8A is one example of an amino-functionalized PBDE compound and that the amino group may be positioned at an alternative location on the phenyl ring (e.g., the 5-position meta to the oxygen). Further, it will further be appreciated that alternative amino-functionalized diphenyl ether compounds containing amino groups on both phenyl rings may be also utilized.

FIG. 8A illustrates that the amino-functionalized PBDE compound can be functionalized with a single allyl group in a 1:1 ratio to yield an allyl-PBDE compound having the following structural formula:

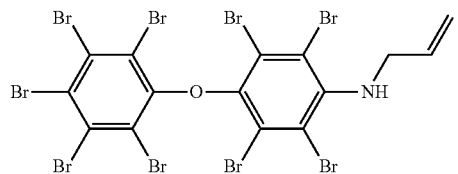 [SMILES: C=CCNc1c(Br)c(Br)c(Oc2c(Br)c(Br)c(Br)c(Br)c2Br)c(Br)c1Br]

Figure 9A:
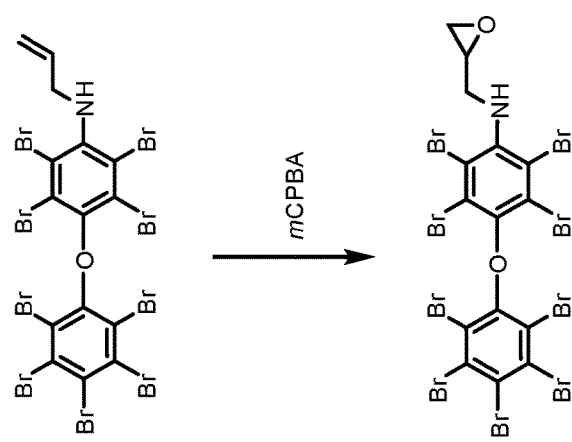
FIGS. 9A and 9B are chemical reaction diagrams illustrating processes for further functionalization of the allyl group of the Amino-PBDE compound depicted in FIG. 8A, according to various embodiments.
Figure 9B:
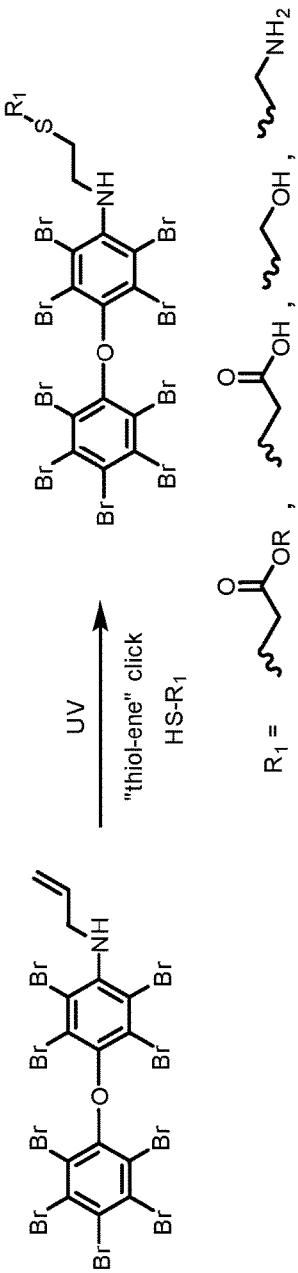

In some embodiments, the allyl group of the allyl-PBDE compound of FIG. 8A may be further functionalized in a similar fashion to FIGS. 3C to 3D, as illustrated and further described herein with respect to FIGS. 9A and 9B.

As a prophetic example, the amino-PBDE compound may be added to a solution of NaH in anhydrous THF, 1,4-dioxane, acetone, or DMF for reaction via nucleophilic substitution chemistry with an allyl chloride (where X=Cl) or an allyl bromide (where X=Br), yielding the allyl-PBDE compound. The allyl halide may be added dropwise at or below ambient temperature and the reaction may be stirred for several at ambient temperature or at reflux. The reaction mixture may be extracted with ethyl acetate, benzene, or toluene. The combined organic extracts may be dried over anhydrous Na₂SO₄ and the solvents removed in vacuo. The crude mixture may be purified by column chromatography over silica gel.

FIG. 8B illustrates that the amino-functionalized PBDE compound can be functionalized with excess allyl halide to yield an allyl-PBDE compound having the following structural formula:

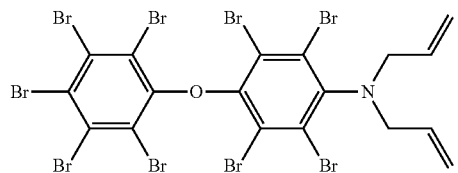

Figure 10A:
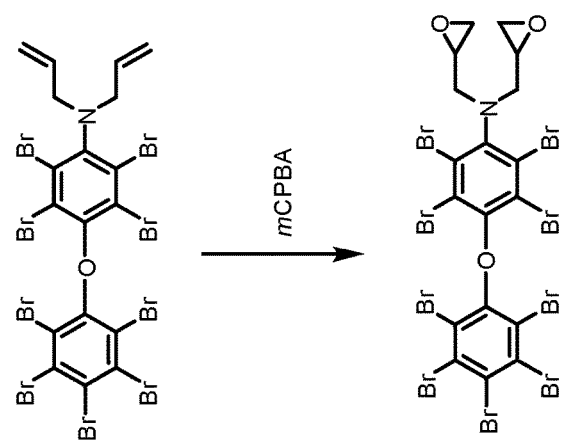
FIGS. 10A and 10B are chemical reaction diagrams illustrating processes for further functionalization of the multiple allyl groups of the Amino-PBDE compound depicted in FIG. 8B, according to various embodiments.
Figure 10B:
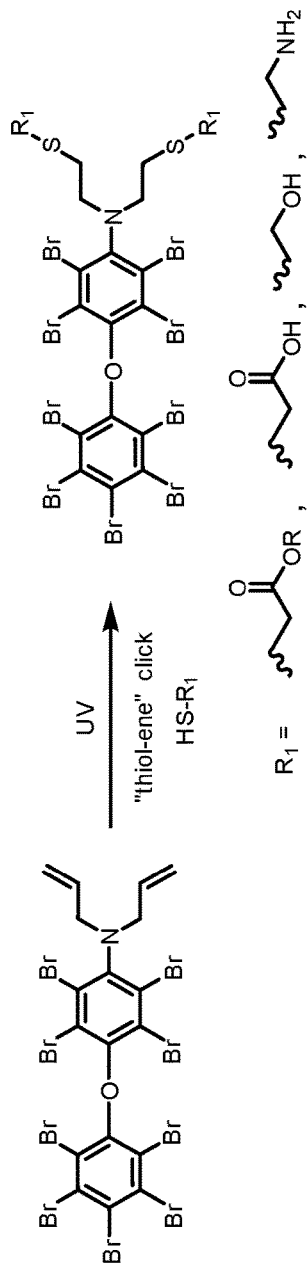

The allyl groups of the allyl-PBDE compound of FIG. 8B may be further functionalized in a similar fashion to FIGS. 3C to 3D, as illustrated and further described herein with respect to FIGS. 10A and 10B.

FIG. 9A is a chemical reaction diagram 900 illustrating a particular embodiment of a process of forming an epoxy-PBDE compound by reacting the allyl-PBDE compound of FIG. 8A with mCPBA to yield an epoxy-PBDE compound having the following structural formula:

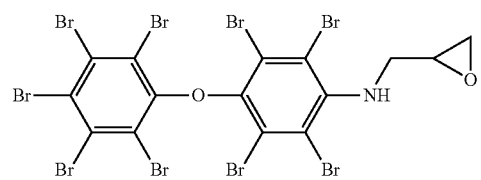 [SMILES: Brc1c(Br)c(Br)c(Oc2c(Br)c(Br)c(NCC3CO3)c(Br)c2Br)c(Br)c1Br]

In a particular embodiment, the epoxy-PBDE compound of FIG. 9A may be formed in a similar manner to that previously described herein with respect to FIG. 3C.

FIG. 9B is a chemical reaction diagram 910 depicting a particular embodiment of a process illustrating that the allyl-PBDE compound of FIG. 8A can be reacted via "thiol-ene" click chemistry with thiol compounds (HS-R$_1$) where R$_1$ may represent a functional group such as an ester group, a carboxylic acid group, a hydroxyl group, or an amine group (among other alternatives). The right side of FIG. 9B illustrates a functionalized PBDE compound having the following generic structural formula:

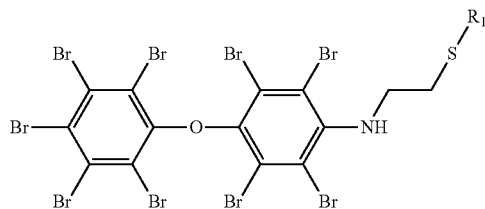

In a particular embodiment, the functionalized PBDE compound of FIG. 9B may be formed using "thiol-ene" click chemistry similar to that previously described herein with respect to FIG. 3D.

Thus, FIGS. 9A and 9B illustrate an example of a process of utilizing an allyl-PBDE compound for functionalization with various functional groups. The various functional groups enables covalent bonding to a material in which it is embedded, thereby mitigating "leach out" associated with existing polybrominated diphenyl-based flame retardant compounds, such as decabromodiphenyl ether and decabromodiphenyl ethane.

FIG. 10A is a chemical reaction diagram 1000 illustrating a particular embodiment of a process of forming an epoxy-PBDE compound by reacting the allyl-PBDE compound of FIG. 8B with mCPBA to yield an epoxy-PBDE compound having the following structural formula:

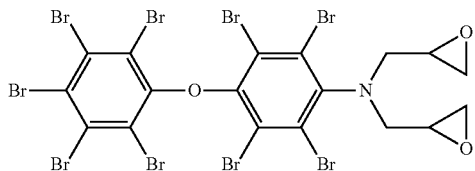 [SMILES: Brc1c(Br)c(Br)c(Oc2c(Br)c(Br)c(N(CC3CO3)CC3CO3)c(Br)c2Br)c(Br)c1Br]

In a particular embodiment, the epoxy-PBDE compound of FIG. 10A may be formed in a similar manner to that previously described herein with respect to FIG. 3C.

FIG. 10B is a chemical reaction diagram 1010 depicting a particular embodiment of a process illustrating that the allyl-PBDE compound of FIG. 8B can be reacted via "thiol-ene" click chemistry with thiol compounds (HS-R$_1$) where R$_1$ may represent a functional group such as an ester group, a carboxylic acid group, a hydroxyl group, or an amine group (among other alternatives). The right side of FIG. 10B illustrates a functionalized PBDE compound having the following generic structural formula:

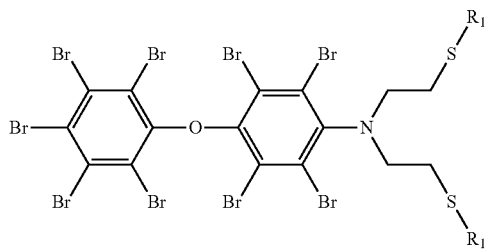

In a particular embodiment, the functionalized PBDE compound of FIG. 10B may be formed using "thiol-ene" click chemistry similar to that previously described herein with respect to FIG. 3D.

Thus, FIGS. 10A and 10B illustrate an example of a process of utilizing an allyl-PBDE compound for functionalization with various functional groups. The various functional groups enables covalent bonding to a material in which it is embedded, thereby mitigating "leach out" associated with existing polybrominated diphenyl-based flame retardant compounds, such as decabromodiphenyl ether and decabromodiphenyl ethane.

Figure 11:
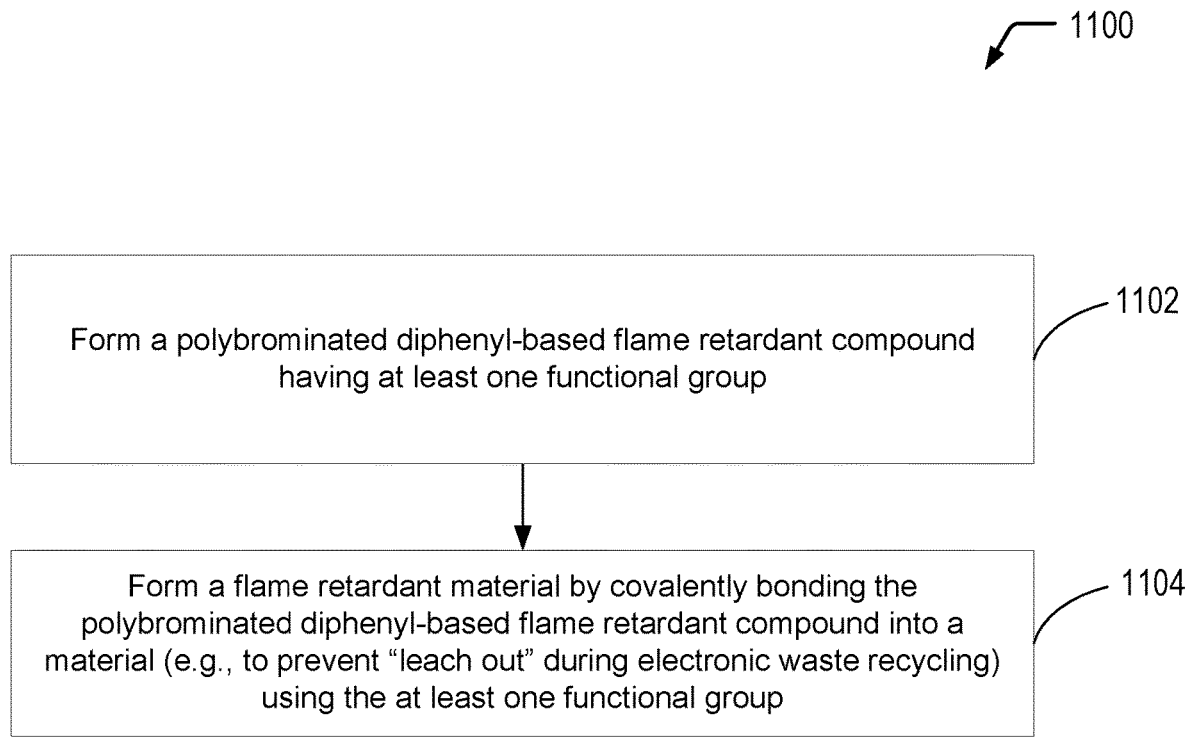
FIG. 11 is a flow diagram illustrating a particular embodiment of a process of forming a flame retardant material by utilizing a functionalized polybrominated diphenyl-based flame retardant compound for covalent bonding into a material.

Referring to FIG. 11, a flow diagram illustrates a particular embodiment of a process 1100 of forming a flame retardant material by utilizing a functionalized polybrominated diphenyl-based flame retardant compound of the present disclosure for covalent bonding of the compound into a material.

The process 1100 includes forming a polybrominated diphenyl-based flame retardant compound having at least one functional group, at 1102. For example, the polybrominated diphenyl-based flame retardant compound having at least one functional group may correspond to any of the functionalized PBDE compounds formed according to the processes described herein with respect to FIGS. 1, 2A to 2D, 3A to 3D, 4A to 4D, 5A to 5F, 6A to 6D, 7A to 7D, 8A/B, 9A/B, and 10A/B.

The process 1100 includes initiating a chemical reaction to covalently bond the polybrominated diphenyl-based flame retardant compound into a material, at 1104. The various functional groups enables covalent bonding to a material in which it is embedded, thereby mitigating "leach out" associated with existing polybrominated diphenyl-based flame retardant compounds, such as decabromodiphenyl ether and decabromodiphenyl ethane.

It will be understood from the foregoing description that modifications and changes may be made in various embodiments of the present invention. The descriptions in this specification are for purposes of illustration only and are not to be construed in a limiting sense. The scope of the present invention is limited only by the language of the following claims.

What is claimed is:

1. A process of forming a flame retardant material, the process comprising:

forming a functionalized polybrominated diphenyl-based flame retardant compound having the following structural formula:

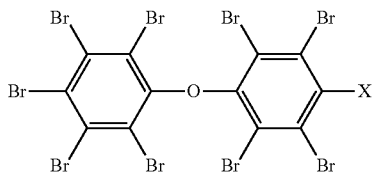

wherein X corresponds to a functional group comprising at least one moiety selected from the group consisting of an ester group, a carboxylic acid group, an amine group, a vinyl group, an aryl group, an acyl group, an epoxy group, a copper atom, a thiyl group, and a secondary alcohol group; and forming a flame retardant material by covalently bonding the functionalized polybrominated diphenyl-based flame retardant compound into a material using the functional group.

2. The process of claim 1, wherein the functionalized polybrominated diphenyl-based flame retardant compound has the following structural formula:

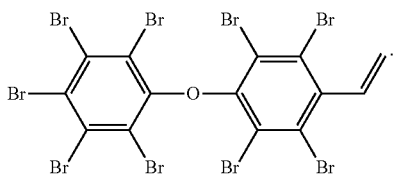 [SMILES: C=Cc1c(Br)c(Br)c(Oc2c(Br)c(Br)c(Br)c(Br)c2Br)c(Br)c1Br]

3. The process of claim 1, wherein the functionalized polybrominated diphenyl-based flame retardant compound has the following structural formula:

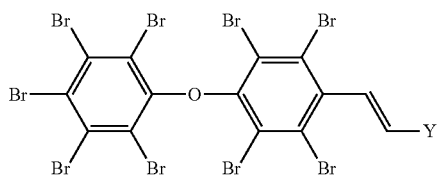

wherein Y corresponds to a functional group selected from the group consisting of: an ester group, a carboxylic acid group, and a nitrile group.

4. The process of claim 1, wherein the functionalized polybrominated diphenyl-based flame retardant compound has the following structural formula:

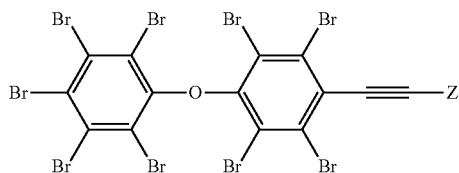

wherein Z corresponds to a functional group comprising a moiety selected from the group consisting of a vinyl group and an aryl group.

5. The process of claim 1, wherein the functionalized polybrominated diphenyl-based flame retardant compound has the following structural formula:

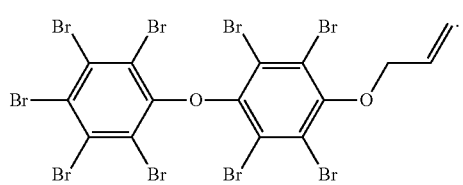 [SMILES: C=CCOc1c(Br)c(Br)c(Oc2c(Br)c(Br)c(Br)c(Br)c2Br)c(Br)c1Br]

6. The process of claim 1, wherein the functionalized polybrominated diphenyl-based flame retardant compound has the following structural formula:

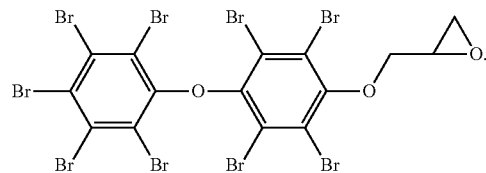 [SMILES: Brc1c(Br)c(Br)c(Oc2c(Br)c(Br)c(OCC3CO3)c(Br)c2Br)c(Br)c1Br]

7. The process of claim 1, wherein the functionalized polybrominated diphenyl-based flame retardant compound has the following structural formula:

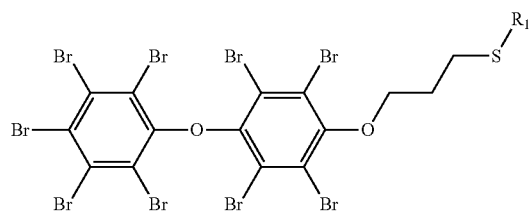

wherein $R_1$ corresponds to a functional group comprising a moiety selected from the group consisting of: an ester group, a carboxylic acid group, a hydroxyl group, and an amine group.

8. The process of claim 1, wherein the functionalized polybrominated diphenyl-based flame retardant compound has the following structural formula:

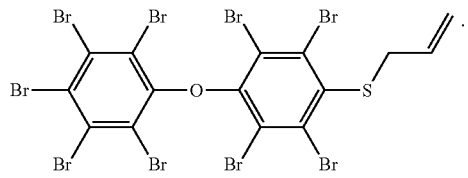 [SMILES: C=CCSc1c(Br)c(Br)c(Oc2c(Br)c(Br)c(Br)c(Br)c2Br)c(Br)c1Br]

9. The process of claim 1, wherein the functionalized polybrominated diphenyl-based flame retardant compound has the following structural formula:

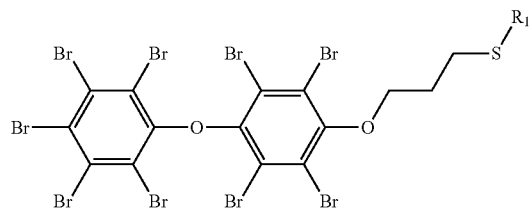

wherein R₁ corresponds to a functional group comprising a moiety selected from the group consisting of: an ester group, a carboxylic acid group, a hydroxyl group, and an amine group.

10. The process of claim 1, wherein the functionalized polybrominated diphenyl-based flame retardant compound is an organocuprate compound having the following structural formula:

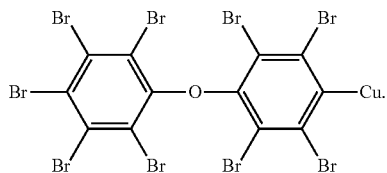

11. The process of claim 1, wherein the functionalized polybrominated diphenyl-based flame retardant compound has the following structural formula:

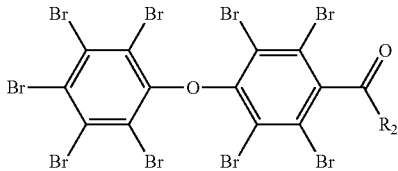

wherein R₂ corresponds to an alkyl group or an aryl group.

12. The process of claim 1, wherein the functionalized polybrominated diphenyl-based flame retardant compound has the following structural formula:

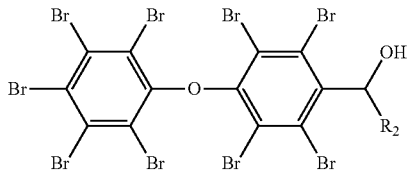

wherein R₂ corresponds to an alkyl group or an aryl group.

13. The process of claim 1, wherein the functionalized polybrominated diphenyl-based flame retardant compound has the following structural formula:

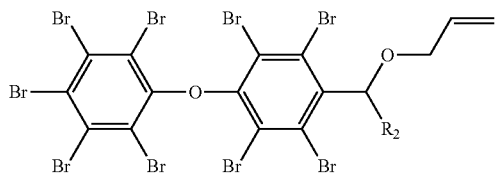

wherein R₂ corresponds to an alkyl group or an aryl group.

14. The process of claim 1, wherein the functionalized polybrominated diphenyl-based flame retardant compound has the following structural formula:

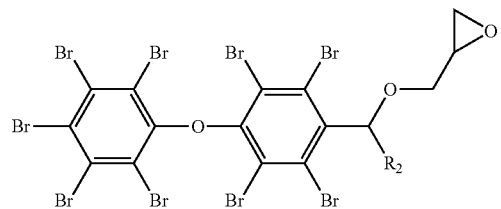

wherein R₂ corresponds to an alkyl group or an aryl group.

15. The process of claim 1, wherein the functionalized polybrominated diphenyl-based flame retardant compound has the following structural formula:

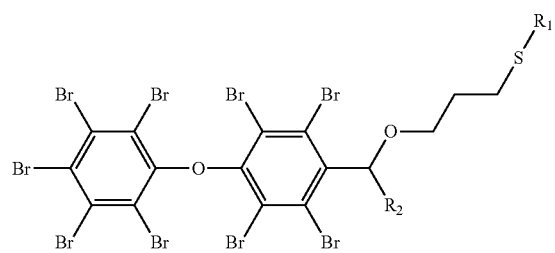

wherein R₁ corresponds to a functional group comprising a moiety selected from the group consisting of: an ester group, a carboxylic acid group, a hydroxyl group, and an amine group, and wherein R₂ corresponds to an alkyl group or an aryl group.

16. The process of claim 1, wherein the functionalized polybrominated diphenyl-based flame retardant compound has the following structural formula:

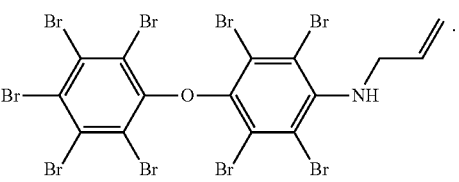

17. The process of claim 1, wherein the functionalized polybrominated diphenyl-based flame retardant compound has the following structural formula:

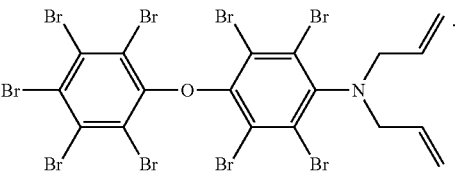 [SMILES: C=CCN(CC=C)c1c(Br)c(Br)c(Oc2c(Br)c(Br)c(Br)c(Br)c2Br)c(Br)c1Br]

18. A process of forming a polybrominated flame retardant compound, the process comprising:

forming an organocuprate compound having the following structural formula:

25

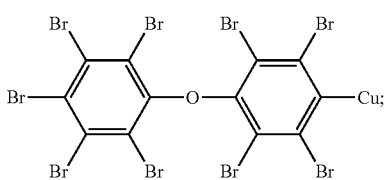

and
utilizing the organocuprate compound to form a polybrominated flame retardant ketone compound having the following structural formula:

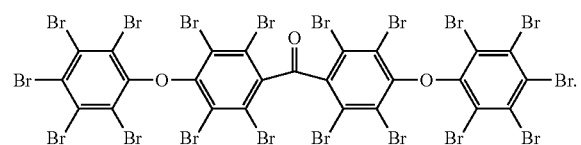

19. The process of claim 18, further comprising utilizing the polybrominated flame retardant ketone compound to

26 form a hydroxyl-functionalized polybrominated flame retardant compound having the following structural formula:

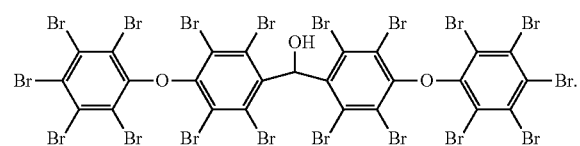

20. An organocuprate compound having the following structural formula:

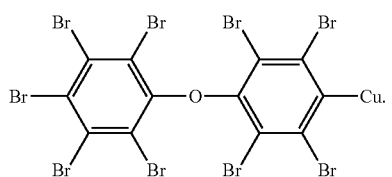

* * * * *